US006866137B2

(12) United States Patent
Ohiro et al.

(10) Patent No.: US 6,866,137 B2
(45) Date of Patent: Mar. 15, 2005

(54) ARTICLE TURNING-ROUND APPARATUS

(75) Inventors: Masaya Ohiro, Kagawa-ken (JP);
Norikatsu Kushida, Kagawa-ken (JP);
Hiroki Yamamoto, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 10/712,292

(22) Filed: Nov. 14, 2003

(65) Prior Publication Data

US 2004/0144619 A1 Jul. 29, 2004

(30) Foreign Application Priority Data

Nov. 18, 2002 (JP) ........................................ 2002-333357

(51) Int. Cl.[7] .............................................. B65G 47/24
(52) U.S. Cl. .................. 198/374; 198/377.01; 198/394; 198/399; 198/411
(58) Field of Search ................................ 198/374, 379, 198/382, 384, 394, 399, 411

(56) References Cited

U.S. PATENT DOCUMENTS

| | | | | |
|---|---|---|---|---|
| 3,847,273 A | * | 11/1974 | Buhayar | 198/377.07 |
| 5,988,354 A | * | 11/1999 | Spatafora et al. | 198/471.1 |
| 6,116,317 A | * | 9/2000 | Tharpe et al. | 198/374 |
| 6,155,775 A | * | 12/2000 | Depinet et al. | 198/399 |
| 6,604,623 B2 | * | 8/2003 | Sumi et al. | 198/377.08 |
| 6,722,494 B2 | * | 4/2004 | Nakakado | 198/377.01 |

FOREIGN PATENT DOCUMENTS

JP             8-310705         11/1996

* cited by examiner

Primary Examiner—Gene O. Crawford
(74) Attorney, Agent, or Firm—Lowe Hauptman & Berner, LLP

(57) ABSTRACT

The present invention aims to provide an article turning-round apparatus improved so that a series of articles can be successively turned round at a high velocity and there is no restriction imposed on the positions at which the articles are loaded and unloaded.

An article turning-round apparatus comprises a rotary table adapted to be rotated by means of a first shaft, a plurality of load-carrying tables mounted on the rotary table along a peripheral zone thereof, a first conveyor belt assembly serving to convey diapers to a first station and a second conveyor belt assembly serving to convey the diapers away from a second station, wherein each of the load-carrying tables consists of a first load-carrying table adapted to move along the peripheral zone of the rotary table and a second load-carrying table adapted to rotate around its own axis in the peripheral zone of the rotary table while these second load-carrying tables move along the peripheral zone of the rotary table and wherein the articles are loaded, in the first station, on these load-carrying tables and the second load-carrying tables are adapted to rotate around their own axes approximately by an angle of 180° in the peripheral zone of the rotary table while these second load-carrying tables move from the first station to the second station.

7 Claims, 15 Drawing Sheets

ARTICLE TURNING-ROUND APPARATUS

RELATED APPLICATIONS

The present application is based on, and claims priority from, Japanese Application Serial Number 2002-333357, filed Nov. 18, 2002, the disclosure of which is hereby incorporated by reference herein in its entirety.

BACKGROUND OF THE INVENTION

The present invention relates to an apparatus adapted to turn round a series of predetermined articles successively.

Japanese Patent Application Publication No. 1996-310705A discloses a work turning-round apparatus proposed, which successively turns round a plurality of works fed at regular intervals by an angle of 90° relative to a direction in which the works are conveyed. These works are held on the apparatus in the course of being turned round.

The work turning-round apparatus disclosed in the above-cited Publication comprises a guide rail presenting a substantially oval profile, an endless conveyor circularly running along the guide rail, a plurality of carriages mounted on the endless conveyor and moving on the guide rail, table bases rotatably mounted on the carriages and work tables mounted on the table bases integrally therewith. The endless conveyor has a loading station and an unloading station for the sheet-like works and a pair of connecting conveyor sections extending between the loading station and the unloading station. In the case of this well-known work turning-round apparatus, rectilinear sections of the guide rail define the loading station and the unloading station, respectively, and curved sections of the guide rail define the connecting conveyor sections, respectively.

With this work turning-round apparatus, the works are held, at the loading station, on the respective work tables of the carriages and travel toward the unloading station through one of the connecting conveyor sections as the endless conveyor runs. Each of the table bases rotates by an angle of 90° relative to the associated carriage around its axis extending in a direction crossing the direction in which the works are conveyed and thereby turns round the work held on the work table by the corresponding angle. At the unloading station, this work is conveyed away from the turning-round apparatus. After the work has been conveyed away from the turning-round apparatus, the table base rotates again by an angle of 90° relative to the associated carriage, at the other of the connecting conveyor sections, around its axis crossing the direction in which the works are conveyed. In this way, each of the works rotates by an angle of 180° while the associated table base makes a circuit of the guide rail.

With the work turning-round apparatus disclosed in the above-cited Publication, the table bases can be rotated along the connecting conveyor sections but can be rotated neither at the loading station nor at the unloading station. This is for the reason that the guide rail rectilinearly extends at the loading and unloading stations and a plurality of the table bases closely lined up along these stations. If it is intended to rotate a pair of the adjacent table bases along the rectilinear sections of the guide rail defined by the loading and unloading stations, these table bases will bump against each other and prevented from smoothly rotating. Along the curved connecting conveyor sections, on the other hand, there is a difference in level between each pair of the adjacent table bases and therefore each of these adjacent table bases can be rotated without any interference with each other.

This work turning-round apparatus is constructed so that the table bases rotate around their own axes along the curved sections of the guide rail (i.e., connecting conveyor sections) and loading as well as unloading of the works is carried out along the rectilinear sections of the guide rail (i.e., the loading station and the unloading station). Thus a restriction is imposed on the positions on the apparatus at which the works are loaded and are unloaded.

In this work turning-round apparatus, the carriages travel on the guide rail by means of guide rollers mounted on these carriages and a plurality of the table bases rotate on their own axes while these table bases travel on the guide rail. Such construction not only complicates the structure of the apparatus but also is unsuitable for the purpose of turning round the works at a high velocity.

SUMMARY OF THE INVENTION

It is an object of the present invention to provide an article turning-round apparatus improved so that a series of articles can be successively turned round at a high velocity and there is no restriction imposed on the positions at which the articles are loaded and unloaded.

According to the present invention, there is provided an article turning-round apparatus provided with first and second stations at which a plurality of disposable wearing articles each having, in addition to front and rear waist regions opposed to each other, a waist-surrounding upper end zone and a crotch bottom zone, are successively loaded and unloaded, respectively, and adapted to successively turn round the articles moving from the first station to the second station.

The improvement according to the present invention is characterized by that the turning-round apparatus comprises a rotary base adapted to be rotated by means of a first shaft and provided along a peripheral zone thereof with the first and second stations and a plurality of load-carrying tables arranged at regular intervals along the peripheral zone, the load-carrying tables being adapted to carry thereon the articles of which the front or rear waist regions are held in contact with the load-carrying tables and the waist-surrounding upper end zones are lined up in a predetermined direction; the load-carrying tables comprise first load-carrying tables adapted to move along the peripheral zone of the rotary base and second load-carrying tables mounted on the rotary base so as to be rotated by respective second shafts extending in an axial direction of the first shaft, the second load-carrying tables being adapted to be rotated around their own axes in the peripheral zone of the rotary base while the second load-carrying tables move along the peripheral zone of the rotary base as the rotary base rotates, the first and second load-carrying tables being alternately arranged so that each of the second load-carrying tables be interposed between each pair of the first load-carrying tables; and the first and second load-carrying tables are successively loaded with the articles as soon as the first and second load-carrying tables alternately reach the first station as the rotary base rotates and the second load-carrying tables rotate in the peripheral zone of the rotary base on their own axes substantially by an angle of 180° relative to the first load-carrying tables while the second load-carrying tables move along the peripheral zone of the rotary base from the first station to the second station.

The present includes the following embodiments.

The first and second load-carrying tables include a first suction mechanism functioning to hold the articles on the first and second load-carrying tables under a suction effect, the first load-carrying tables move along the peripheral zone of the rotary base from the first station to the second station together with the articles held thereon under the suction effect, on one hand, and the second load-carrying tables rotating around their own axes together with the articles held thereon under the suction effect in the peripheral zone of the rotary base while the second load-carrying tables move along the peripheral zone of the rotary base together with the articles held thereon under the suction effect from the first station to the second station, on the other hand.

The article turning-round apparatus further comprises a first conveyor belt assembly adapted to convey the articles at regular intervals to the first station of the rotary base so that each pair of the adjacent articles may have respective waist-surrounding upper end zones lined up with each other and a second conveyor belt assembly adapted to convey the articles away from the second station of the rotary base at regular intervals so that each pair of the adjacent articles may have respective waist-surrounding upper end zones and respective crotch bottom zones lined up with each other.

The article turning-round apparatus further comprises a first conveyor belt assembly adapted to convey the articles at regular intervals to the first station of the rotary base so that each pair of adjacent the articles may have respective waist-surrounding upper end zones and respective crotch bottom zones opposed to each other and a second conveyor belt assembly adapted to convey the articles away from the second station of the rotary base at regular intervals so that each pair of the adjacent articles may have respective waist-surrounding upper end zones opposed to each other.

The first conveyor belt assembly includes a second suction mechanism adapted to hold the articles on the first conveyor belt under a suction effect and, when the first and second load-carrying tables come face to face with the first conveyor belt assembly, the first suction mechanism effectively functions against the effect of the second suction mechanism to transfer the articles from the first conveyor belt assembly onto the first and second load-carrying tables.

The second conveyor belt assembly includes a third suction mechanism adapted to hold the articles on the second conveyor belt under a suction effect and, when the first and second load-carrying tables come face to face with the second conveyor belt assembly, the third suction mechanism effectively functions against the effect of the first suction mechanism to transfer the articles from the first and second load-carrying tables onto the second conveyor belt assembly.

The article is a pull-on disposable diaper comprising a liquid-pervious topsheet facing a wearer's body, a liquid-impervious backsheet facing away from the wearer's body and a liquid-absorbent core interposed between the top- and backsheets and formed with a waist-hole and a pair of leg-holes.

DETAILED DESCRIPTION OF THE PREFERRED EMBODIMENTS

Details of an article turning-round apparatus according to the present invention will be more fully understood from the description predetermined hereunder with reference to the accompanying drawings.

Figure 1:
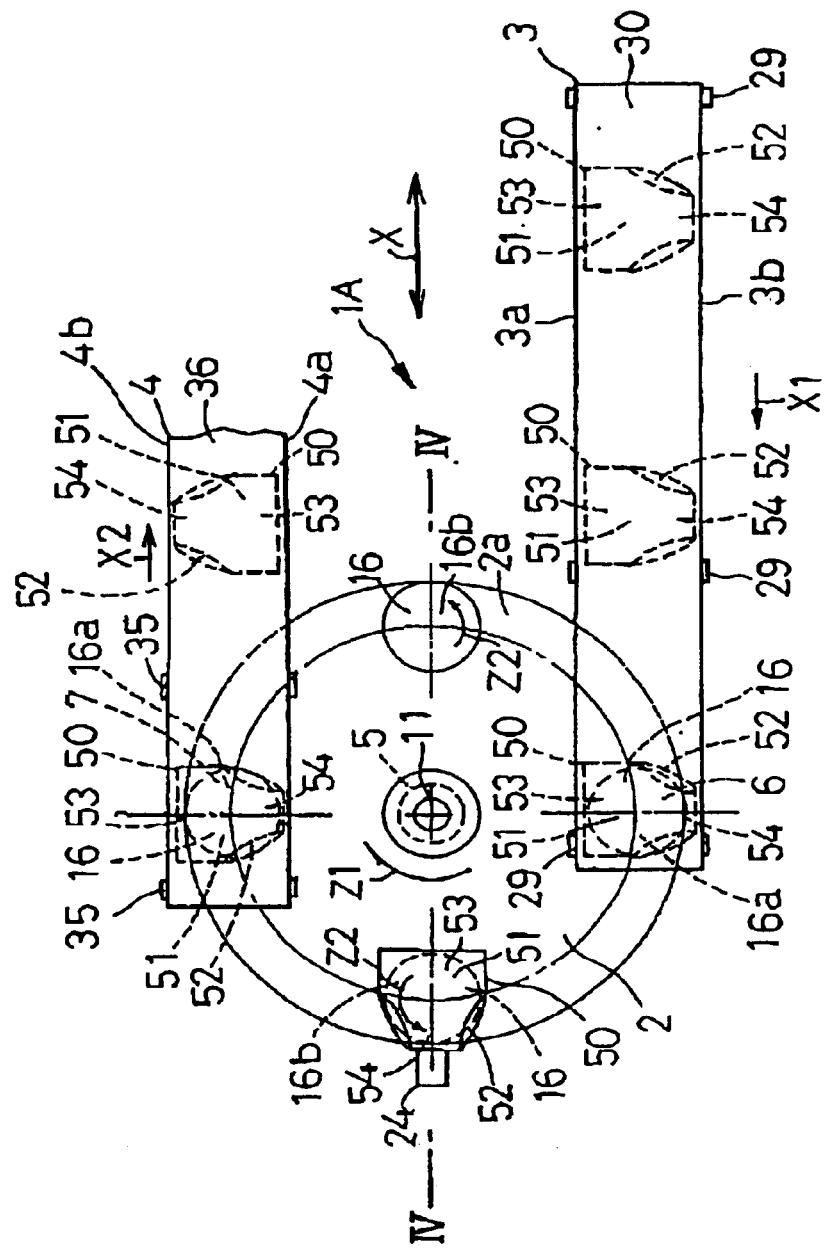
FIG. 1 is a top view showing an article turning-round apparatus having a timing belt not shown.
Figure 2:
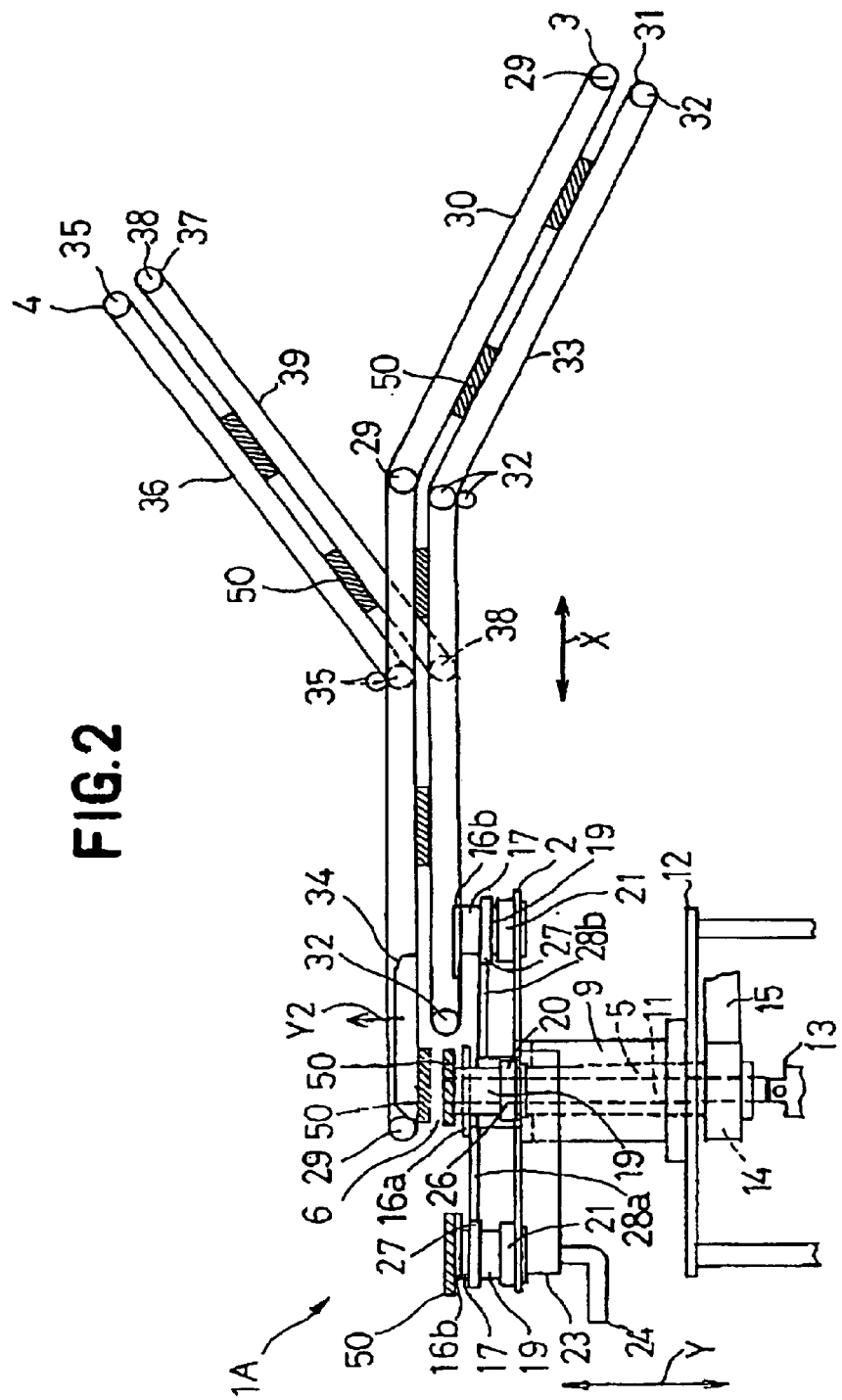
FIG. 2 is a side view showing the turning-round apparatus as viewed from the side of a first station.
Figure 3:
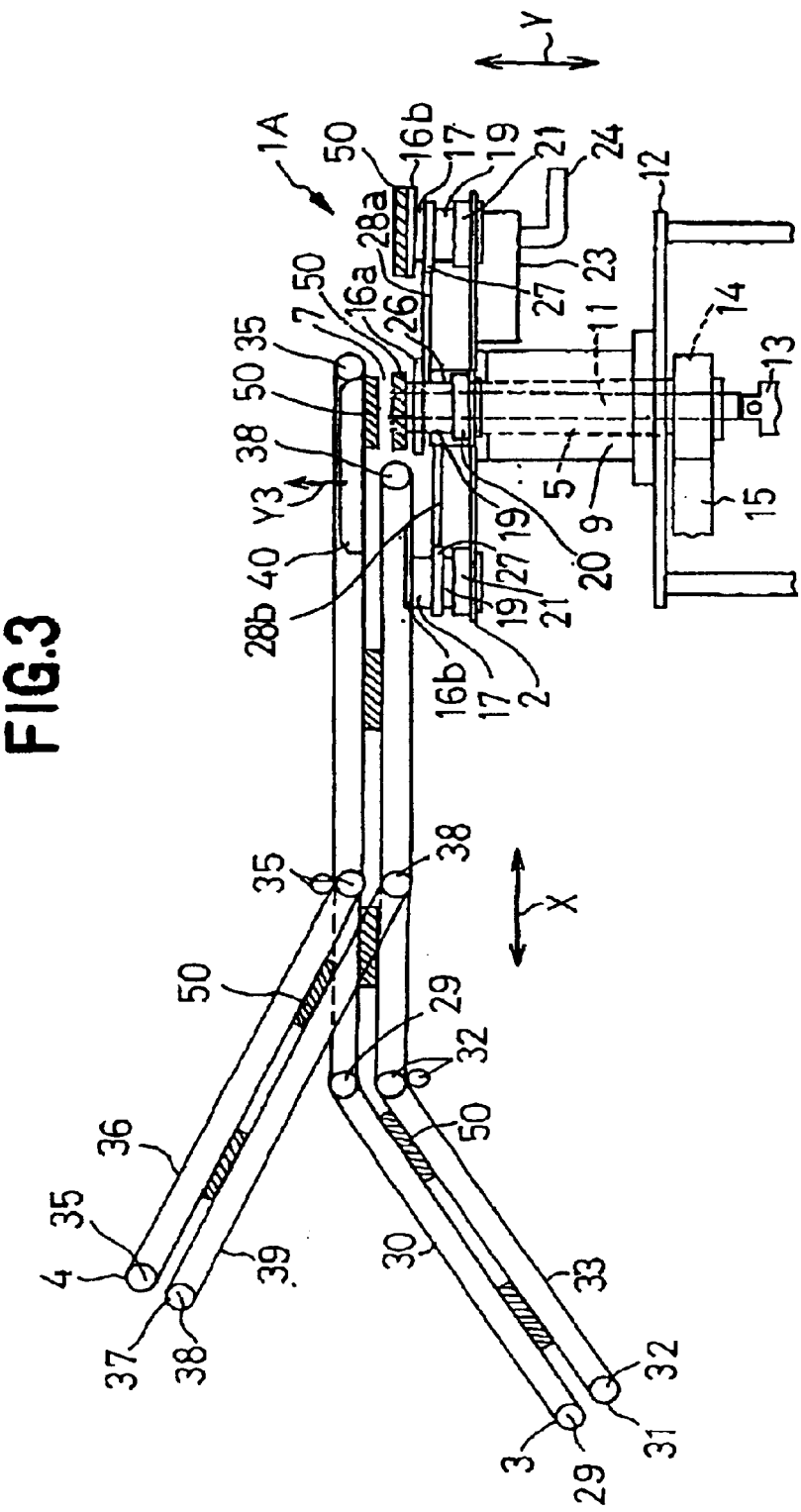
FIG. 3 is a side view showing the turning-round apparatus as viewed from the side of a second station.
Figure 4:
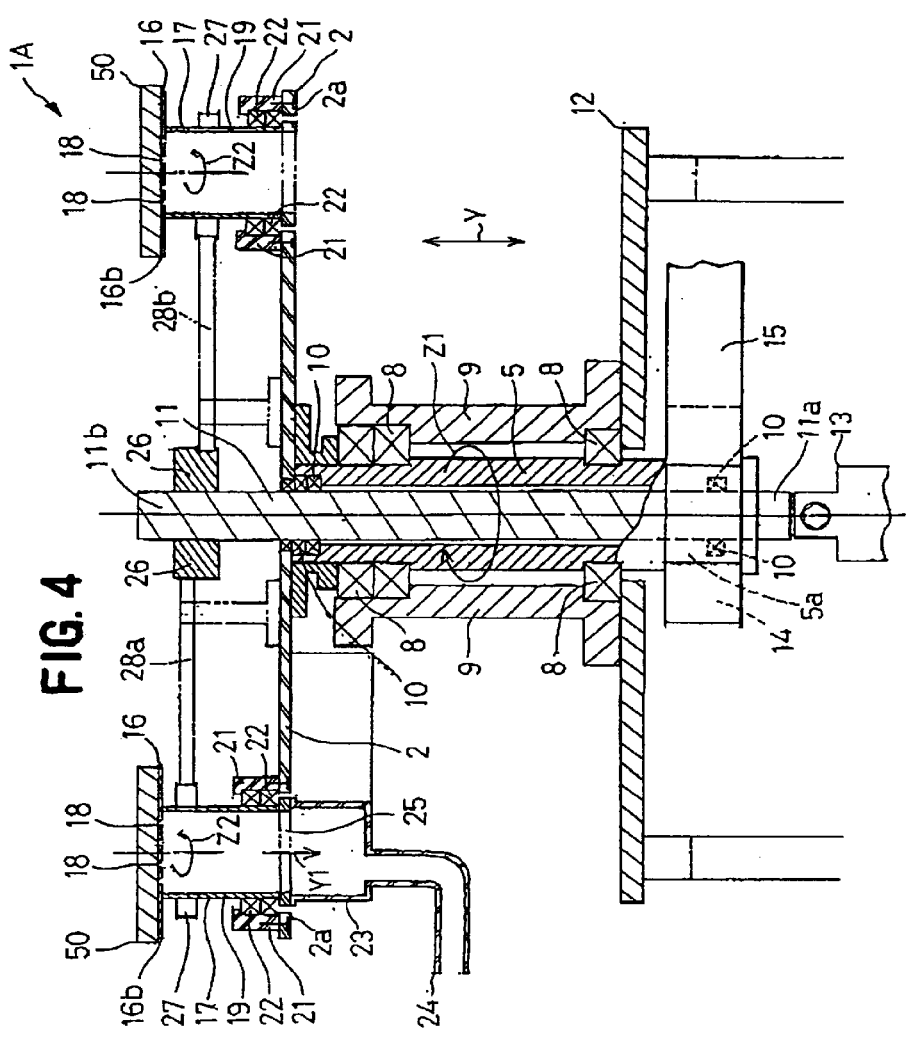
FIG. 4 is a sectional view taken along a line IV—IV in FIG. 1, showing the turning-round apparatus as viewed from the side of the first station.

FIG. 1 is a top view showing a article turning-round apparatus 1A having timing belts not shown, FIG. 2 is a side view showing the turning-round apparatus 1A as viewed from the side of a first station 6, FIG. 3 is a side view showing the turning-round apparatus 1A as viewed from the side of a second station 7 and FIG. 4 is a sectional view taken along a line IV—IV in FIG. 1, showing the turning-round apparatus 1A as viewed from the side of the first station 6. In FIGS. 1 through 4, a vertical direction is indicated by an arrow Y and a horizontal direction is indicated by an arrow X.

The turning-round apparatus 1A functions to alternately turn round a plurality of disposable diapers 50 (disposable wearing article) continuously manufactured and fed at regular intervals. The turning-round apparatus 1A comprises a rotary table 2 (rotary base) provided with a plurality of load-carrying tables 16, a first conveyor belt assembly 3 serving to carry the diapers 50 onto the rotary table 2 and a second conveyor belt assembly 4 serving to carry the diapers 50 away from the rotary table 2.

The rotary table 2 has a first tubular shaft 5 extending in the vertical direction around which the rotary table 2 is rotated. A peripheral zone 2a of the rotary table 2 is provided with the first station 6 at which the diapers 50 are loaded from the first conveyor belt assembly 3 onto the rotary table 2 and the second station 7 at which the diapers 50 are unloaded from the rotary table 2 onto the second conveyor belt assembly 4. The second station 7 corresponds to a position along the peripheral zone 2a of the rotary table 2 at which the rotary table 2 has been rotated by an angle of 180° from the first station 6 (i.e., the second station 7 is located at an angular distance of 180° from the first station 6). There is provided externally of the rotary table 2 an electric motor (not shown) rotationally driving the first shaft 5.

A part of the first shaft 5 extending downward from the rotary table 2 is covered with a tubular stationary frame 9 and bearings 8 are interposed between these first shaft 5 and tubular stationary frame 9. Within the first shaft 5, a stationary shaft 11 extends with bearings 10 interposed therebetween. The stationary frame 9 is fixed to a pedestal 12. The first shaft 5 and the stationary shaft 11 rise above the pedestal 12. The bearings 8 are interposed between the outer peripheral surface of the first shaft 5 and the inner peripheral surface of the stationary frame 9 and the bearings 10 are interposed between the inner peripheral surface of the first shaft 5 and the outer peripheral surface of the stationary shaft 11. The first shaft 5 rotates between the stationary frame 9 and the stationary shaft 11. The stationary shaft 11 has its lower end 11a connected to a lock member 13 and therefore can not be rotated. The first shaft 5 is provided on its lower end 5a with a pulley 14. Rotation of the electric motor is transmitted by a drive belt 15 passed on the pulley 14 to the first shaft 5. Rotation of the first shaft 5 causes the rotary table 2 to rotate in the same direction as the direction in which the first shaft 5 rotates.

The load-carrying tables 16 are mounted on the upper surface of the rotary table 2 along the peripheral zone 2a at regular intervals in the circumferential direction. The load-carrying tables 16 comprise first load-carrying tables 16a stationarily mounted on the rotary table 2 and second load-carrying tables 16b mounted on the rotary table 2 so as to be rotatable around second shafts 17 extending in an axial direction of the first shaft 5. These first and second load-carrying tables 16a, 16b are alternately arranged along the peripheral zone 2a of the rotary table 2 so that each of the second load-carrying tables 16b be interposed between each pair of the adjacent first load-carrying tables 16a, 16a. The first load-carrying tables 16a go round along the peripheral zone 2a as the rotary table 2 rotates. The second load-carrying tables 16b rotate on their own axes while these tables 16b go round along the peripheral zone 2a of the rotary table 2 as the rotary table 2 rotates.

Each of these first and second load-carrying tables 16a, 16b has a first suction mechanism serving to hold the diaper 50 under a suction effect and formed with a plurality of openings extending through the first and second load-carrying tables 16a, 16b between their upper and lower surfaces. The first and second load-carrying tables 16a, 16b are provided with a cylindrical duct 19 extending downward from each of these first and second load-carrying tables 16a, 16b.

The ducts 19 of the first load-carrying tables 16a are fixed to support members 20 mounted on the rotary table 2. The ducts 19 of the second load-carrying tables 16b are supported by support members 21 mounted on the rotary table 2 by means of bearings 22. The ducts 19 define the second shafts 17 for the respective second load-carrying tables 16b and rotate together with these second load-carrying tables 16b.

A suction box 23 underlies the rotary table 2 The suction box 23 is provided with a duct 24. The suction box 23 extends along the peripheral zone 2a of the rotary table 2 from the first station 6 to the second station 7. The suction box 23 is provided on its top with an opening 25. The rotary table 2 overlies the opening 25. The suction box 23 constantly sucks air flow through the duct 24.

In each of the first suction mechanisms, rotation of a fan (not shown) causes air to be sucked through the duct 19 downward in a direction indicated by an arrow Y1 in FIG. 4 so that a pressure within the duct 19 may be maintained at a negative pressure (an air pressure approximates vacuum). Specifically, the air is sucked through the openings 18 of the first and second load-carrying tables 16a, 16b into the respective ducts 19 and flows from the suction box 23 toward the ducts 24 as the fan rotates. Consequently, a sucking force is generated so as to be exerted on the first and second load-carrying tables 16a, 16b from upper surfaces toward lower surfaces thereof.

An upper end 11b of the stationary shaft 11 and the second shafts 17 (i.e., the ducts 19) of the second load-carrying tables 16b are provided thereon with pulleys 26, 27. Timing belts 28a, 28b are passed on these pulleys 26, 27. Specifically, these belts 28a, 28b are passed on the pulleys 26, 27 in open fashion. Clockwise rotation of the rotary table 2 in a direction indicated by an arrow Z1 causes the belts 28a, 28b to travel along the periphery of the pulley 26. Thus a turning force is transmitted by the belts 28a, 28b to the pulley 27 and thereby the second load-carrying tables 16b counterclockwise rotate together with the respective ducts 19 around the axes of these second load-carrying tables 16b in a direction indicated by an arrow Z2.

In the case of this turning-round apparatus 1A, a pair of the first load-carrying tables 16a and a pair of the second load-carrying tables 16b are mounted on the rotary table 2. A line segment extending from the central point of the first shaft 5 to the central point of the first load-carrying table 16a and a line section extending from the central point of the first shaft 5 to the central point of the second load-carrying table 16b include an angle of 90° therebetween, so these load-carrying tables 16a, 16b are located along the peripheral zone 2a of the rotary table 2 at the angular intervals of 90°. It should be noted here that the total number of these load-carrying tables 16a, 16b are not limited to four (4) as illustrated so far as the number of the first load-carrying tables 16a and the number of the second load-carrying tables 16b are respectively plural and equal to each other.

If three first load-carrying tables 16a and three second load-carrying tables 16b are mounted on the rotary table 2, the line segment extending from the central point of the first shaft 5 to the central point of the first load-carrying table 16a and the line section extending from the central point of the first shaft 5 to the central point of the second load-carrying table 16b will include an angle of 60° therebetween, so these load-carrying tables 16a, 16b will be located along the peripheral zone 2a of the rotary table 2 at the angular intervals of 60°. If four first load-carrying tables 16a and four second load-carrying tables 16b are mounted on the rotary table 2, the line segment extending from the central point of the first shaft 5 to the central point of the first load-carrying table 16a and the line section extending from the central point of the first shaft 5 to the central point of the second load-carrying table 16b will include an angle of 45° therebetween, so these load-carrying tables 16a, 16b will be located along the peripheral zone 2a of the rotary table 2 at the angular intervals of 45°.

As will be seen in FIG. 2, the first conveyor belt assembly 3 comprises a plurality of belt pulleys 29 and a belt 30 passed on these belt pulleys 29. The belt 30 circularly runs as the belt pulleys 29 rotate. Below the first conveyor belt assembly 3, a third conveyor belt assembly 31 is located.

The third conveyor belt assembly 31 comprises a plurality of belt pulleys 32 and a belt 33 passed on these belt pulleys 32. The belt 33 circularly runs in synchronization with the belt 30 as the belt pulleys 32 rotate. The first conveyor belt assembly 3 extends in the horizontal direction toward the peripheral zone 2a of the rotary table 2 so as to reach the first station 6 on the upper surface of the rotary table 2. The third conveyor belt assembly 31 extends in the horizontal direction toward the peripheral zone 2a of the rotary table 2 so as to terminate short of the peripheral zone 2a of the rotary table 2.

The first conveyor belt assembly 3 is provided with a second suction mechanism serving to suck the diapers 50 and thereby to hold them. The belt 30 of the first conveyor belt assembly 3 is formed with a plurality of openings (not shown) extending through the belt 30 between its upper and lower surfaces. A suction box 34 is interposed between upper and lower pathways of the belt 30. This suction box 34 extends from the vicinity of the first station 6 over this first station 6. The suction box 34 is formed with a plurality openings (not shown) extending through its lower surface.

In the second suction mechanisms, rotation of a fan (not shown) causes air to be sucked into the suction box 34 in a direction indicated by an arrow Y2 in FIG. 2. Specifically, the air flows through the openings of the belt 30 from the outer surface to the inner surface of the belt 30 and then into the suction box 34 through the openings of the suction box 34 as the fan rotates. Consequently, a sucking force is generated so as to be exerted on the belt 30 from its outer surface toward its inner surface.

The diapers 50 are held between the first conveyor belt assembly 3 and the third conveyor belt assembly 31 and conveyed by these conveyor belt assemblies 3, 31 at the regular intervals toward the first station 6 of the rotary table 2 as indicated by the arrow X in FIG. 1. These diapers 50 have their front waist regions 51 held in contact with the first conveyor belt assembly 3, the rear waist regions 52 held in contact with the third conveyor belt assembly 31, the waist-surrounding upper end zones 53 lying on the side of the inner side edge 3a of the conveyor belt assembly 3 and the crotch bottom zones 54 lying on the side of the outer edge 3b of the conveyor belt assembly 3. Along the first and third conveyor belt assemblies 3, 31, the waist-surrounding upper end zones 53 of these diapers 50 line up in the horizontal direction and the crotch bottom zones 54 of these diapers 50 also line up in the horizontal direction. The diapers 50 are successively held on the first conveyor belt assembly 3 under the effect of the second suction mechanism as the diapers 50 get nearer to the first station 6.

It should be understood that the third conveyor belt assembly 31 may be eliminated from this turning-round apparatus 1A. In this case, the suction box 34 interposed between the upper and lower pathways of the belt 30 will cover a substantially entire area of the first conveyor belt assembly 3 so that the diapers 50 can be reliably held by the first conveyor belt assembly 3 under the suction effect until these diapers 50 successively reach the first station 6.

As will be seen in FIG. 3, the second conveyor belt assembly 4 comprises a plurality of belt pulleys 35 and a belt 36 passed on these belt pulleys 35. The belt 36 circularly runs as the belt pulleys 35 rotate. Below the second conveyor belt assembly 4, a fourth conveyor belt assembly 37 is located. The fourth conveyor belt assembly 37 comprises a plurality of belt pulleys 38 and a belt 39 passed on these belt pulleys 38. The belt 39 circularly runs in synchronization with the belt 36 as the belt pulleys 38 rotate. The second conveyor belt assembly 4 extends in the horizontal direction toward the peripheral zone 2a of the rotary table 2 so as to reach the second station 7 on the upper surface of the rotary table 2. The fourth conveyor belt assembly 37 extends in the horizontal direction toward the peripheral zone 2a of the rotary table 2 so as to terminate short of the peripheral zone 2a of the rotary table 2.

The second conveyor belt assembly 4 is provided with a third suction mechanism serving to suck the diapers 50 and thereby to hold them. The belt 36 of the second conveyor belt assembly 4 is formed with a plurality of openings (not shown) extending through the belt 36 between its upper and lower surfaces. A suction box 40 is interposed between upper and lower pathways of the belt 36. This suction box 40 extends from the vicinity of the second station 7 over this second station 7. The suction box 40 is formed with a plurality openings (not shown) extending through its lower surface.

In the third suction mechanisms, rotation of a fan (not shown) causes air to be sucked into the suction box 40 in a direction indicated by an arrow Y3 in FIG. 3. Specifically, the air flows through the openings of the belt 36 from the outer surface to the inner surface of the belt 36 and then into the suction box 40 through the openings of the suction box 40 as the fan rotates. Consequently, a sucking force is generated so as to be exerted on the belt 36 from its outer surface toward its inner surface.

The diapers 50 are held on the second conveyor belt assembly 4 under the effect of the third suction mechanism associated with the second conveyor belt assembly 4, then held between the second conveyor belt assembly 4 and the fourth conveyor belt assembly 37 and conveyed by these conveyor belt assemblies 4, 37 at the regular intervals away from the rotary table 2 as indicated by the arrow X in FIG. 1 These diapers 50 have their front waist regions 51 held in contact with the second conveyor belt assembly 4 and the rear waist regions 52 held in contact with the fourth conveyor belt assembly 37.

Of each pair of the adjacent diapers 50 on the conveyor belt assembly 4, one diaper has its waist-surrounding upper end zone 53 lying on the side of the inner edge 4a of the conveyor belt assembly 4 and its crotch bottom zone 54 lying on the side of the outer edge 4b of the conveyor belt assembly 4 while the other diaper 50 has its waist-surrounding upper end zone 53 lying on the side of the outer edge 4b of the conveyor belt assembly 4 and its crotch bottom zone 54 lying on the side of the inner edge 4a of the conveyor belt assembly 4. Along the second and fourth conveyor belt assemblies 4, 37, each pair of the adjacent diapers 50 respectively have the waist-surrounding upper end zone 53 and the crotch bottom zone 54 in a line in the horizontal direction.

It should be understood that the fourth conveyor belt assembly 37 may be eliminated from this turning-round apparatus 1A. In this case, the suction box 40 interposed between the upper and lower pathways of the belt 36 will cover a substantially entire area of the second conveyor belt assembly 4 so that the diapers 50 can be reliably held on the second conveyor belt assembly 4 under the suction effect until these diapers 50 are successively conveyed away from the rotary table 2 at the second station 7.

Figure 5:
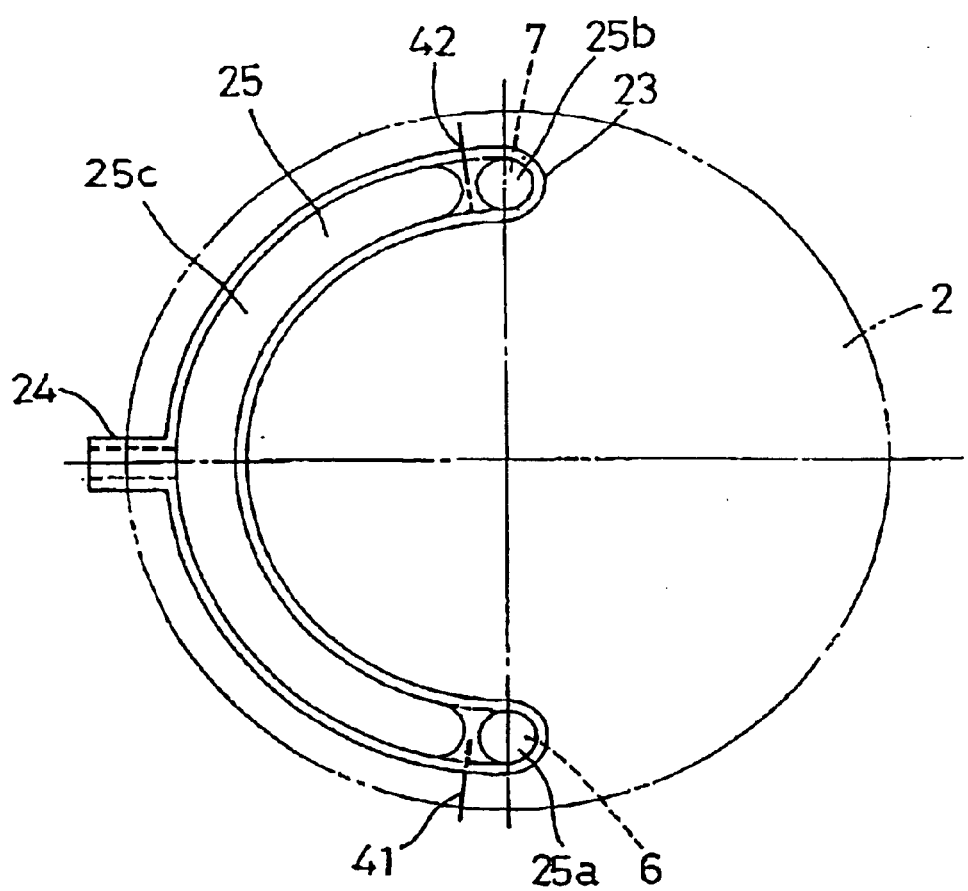
FIG. 5 is a top view showing a suction box.
Figure 6:
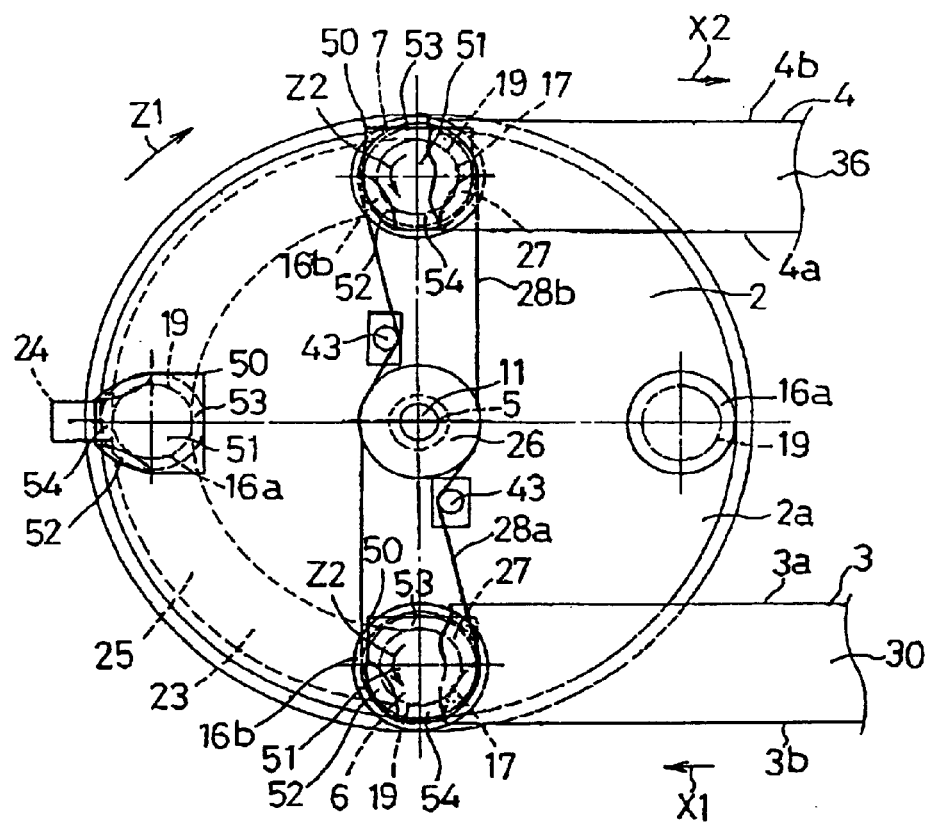
FIG. 6 is a partially cutaway scale-enlarged top view showing the article turning-round apparatus with first and second conveyor belt assemblies.
Figure 7:
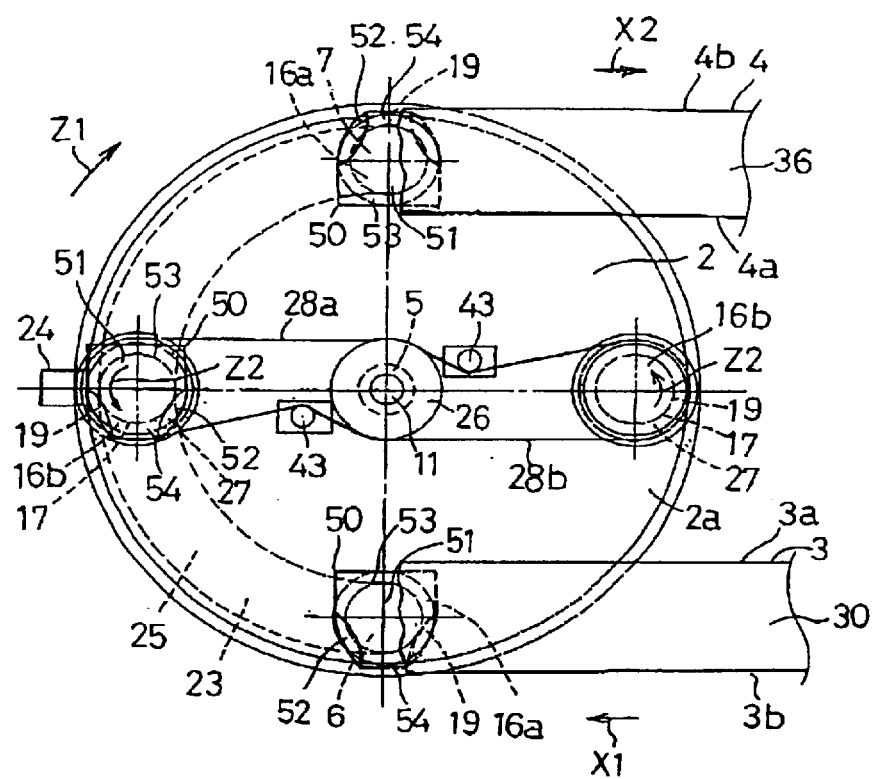
FIG. 7 is a partially cutaway scale-enlarged top view showing the article turning-round apparatus with first and second conveyor belt assemblies.

FIG. 5 is a top view showing a suction box 23 and FIGS. 6 and 7 are scale-enlarged top views showing the article turning-round apparatus 1A with the first and second conveyor belt assemblies 3, 4 partially cut away. In FIG. 5, the rotary table 2 is indicated by chain double-dashed line. In FIGS. 6 and 7, the suction boxes 34, 40 are not shown. FIG. 6 shows the second load-carrying tables 16b having reached the first station 6 and the second station 7 of the rotary table 2, respectively, and FIG. 7 shows the first load-carrying tables 16a having reached the first station 6 and the second station 7 of the rotary table 2, respectively.

The opening 25 of the suction box 23 comprises a first opening 25a located at the first station 6, a second opening 25b located at the second station 7 and a third opening 25c extending between these first and second openings 25a, 25b. While these openings 25a, 25b, 25c of the suction box 23 are substantially closed by the rotary table 2, a slight clearance is defined between the rotary table 2 and the openings 25a, 25b, 25c. A partition plate 41 is inserted between the openings 25a, 25c and a partition plate 42 is inserted between the openings 25b, 25c.

An inner cross-sectional area of the suction box 23 is adjusted by these partition plates 41, 42. The inner cross-sectional area of the suction box 23 is adjustably reduced by these partition plates 41, 42 to reduce a suction force (air suction capacity) at these openings 25a, 25b and the inner cross-sectional area of the suction box 23 is adjustably enlarged by these partition plates 41, 42 to enhance the suction force (air suction capacity) at these openings 25a, 25b. Between the opening 25a and the opening 25c, the inner cross-sectional area of the suction box 23 is enlarged to enhance the suction force at the opening 25a. Between the opening 25b and the opening 25c, the inner cross-sectional area of the suction box 23 is reduced and thereby the suction force at the opening 25b is correspondingly reduced.

The pulley 26 mounted on the stationary shaft 11 and the pulleys 27 mounted on the respective second shafts 17 (the ducts 19) of the second load-carrying tables 16b rotate at a rotational velocity ratio of 1:1. With such setting, when the second load-carrying tables 16b move from the first station 6 to the second station 7 along the peripheral zone 2a of the rotary table 2 approximately by an angle of 180°, a turning force is transmitted to the pulleys 27 through the belt 28a, 28b. Consequently, the second load-carrying tables 16b rotate counterclockwise around their own axes together with the respective ducts 19 approximately by an angle of 180° in the peripheral zone 2a of the rotary table 2. A rotational velocity ratio between the pulley 26 and the pulleys 27 depends on an effective radius ratio between these pulleys 26, 27. Between the pulley 26 and the pulleys 27, there are provided guide wheels 43 adapted to stabilize a tension of the belts 28a, 28b.

Now operation of this turning-round apparatus 1A will be described more in details. In parallel with conveyance of the diapers 50 toward the first station 6 by means of the first and third conveyor belt assemblies 3, 31, the rotary table 2 rotates clockwise (i.e., in the direction Z1) so that any one of the first load-carrying tables 16a or the second load-carrying tables 16b reaches the first station 6. Thereupon the duct 19 comes just above the first opening 25a of the Suction box 23 to establish a communication between the duct 19 and the opening 25a. As a result, the air is sucked through the openings 18 of the first or second load-carrying table 16a, 16b into the duct 19 and thereby the first suction mechanism of the load-carrying table 16a, 16b is actuated. The diaper 50 is thus transferred from the first conveyor belt assembly 3 onto the load-carrying table 16a or 16b under the effect of the first suction mechanism.

The respective diapers 50 are held by the load-carrying tables 16a, 16b under the suction effect with the rear waist regions 52 kept in contact with the upper surfaces of these load-carrying tables 16a, 16b. The first and second load-carrying tables 16a, 16b alternately reach the first station 6 as the rotary table 2 rotates and the diapers 50 are successively transferred onto these load-carrying tables 16a, 16b. At the first station 6, these diapers 50 are carried on the first and second load-carrying tables 16a, 16b with the waist-surrounding upper end zones 53 of these diapers 50 being lined up in a predetermined direction.

In this turning-round apparatus 1A, a suction force of the suction box 23 is previously adjusted to be higher than a suction force of the suction box 34 so that the first suction mechanism can effectively function against the second suction mechanism. As the suction force of the suction box 23 is higher than the suction force of the suction box 34, the first suction mechanism overcomes the effect of against the second suction mechanism and thereby allows the diapers 50 to be quickly transferred from the conveyor belt assembly 3 onto the load-carrying tables 16a, 16b at the first station 6.

The first load-carrying tables 16a and the second load-carrying tables 16b carrying the diapers 50 thereon, respectively, move along the peripheral zone 2a of the rotary table 2 from the first station 6 toward the second station 7 of the rotary table 2. The second load-carrying tables 16b rotate on their own axes in the peripheral zone 2a of the rotary table 2 approximately by an angle of 180° relative to the first load-carrying tables 16a. As a result, the diapers 50 held on the second load-carrying tables 16b, respectively, are turned round approximately by an angle of 180° relative to the diapers 50 held on the first load-carrying tables 16a, respectively.

The diapers 50 are transferred from the respective load-carrying tables 16a, 16b onto the second conveyor belt assembly 4 under the suction effect of the third suction mechanism as the load-carrying tables 16a, 16b reach the second station 7. The diapers 50 are held on the second conveyor belt assembly 4 under the suction effect with the front waist regions 51 thereof kept in contact with the second conveyor belt assembly 4. The first and second load-carrying tables 16a, 16b carrying the diapers 50 thereon, respectively, alternately reach the second station 7 and are successively transferred from the first and second load-carrying tables 16a, 16b onto the conveyor belt assembly 4.

In the case of this turning-round apparatus 1A, the inner cross-sectional area of the suction box 23 is reduced by the partition plate 42 and thereby a suction force of the suction box 40 is previously adjusted to be higher than a suction force of the suction box 23 so that the third suction mechanism can effectively function against the effect of the first suction mechanism. At the second station 7, the duct 19 comes just above the second opening 25c of the suction box 23 in air-communication relationship. However, the suction force of the suction box 40 is higher than the suction force of the section box 23, so the third suction mechanism the effect of the first suction mechanism and thereby allows the diapers 50 to be quickly transferred from the respective load-carrying tables 16a, 16b onto the conveyor belt assembly 4.

After the diapers 50 have been transferred onto the second conveyor belt assembly 4, the load-carrying tables 16a, 16b move from the second station 7 toward the first station 6 as the rotary table 2 rotates. The second load-carrying tables 16b rotate around their own axes approximately by an angle of 180° in the peripheral zone 2a of the rotary table 2 as these second load-carrying tables 16b move along the peripheral zone 2a of the rotary table 2 approximately by an angle of 180°. In other words, the second load-carrying tables 16b rotate around their own axes in the peripheral zone 2a of the rotary table 2 in the course of movement from the second station 7 to the first station 6. More specifically, these second load-carrying tables 16b rotate counterclockwise (i.e., in the direction Z2) around their own axes approximately by an angle of 360° in the peripheral zone 2a of the rotary table 2 as the rotary table 2 rotates clockwise (i.e., in the direction Z1) by an angle of 360° (as the second load-carrying tables 16b start from the first station 6 and return back to the first station 6).

At the first station 6, the diapers 50 held on the first and second load-carrying tables 16a, 16b, respectively, have the waist-surrounding upper end zones 53 facing inward as viewed in the radial direction of the rotary table 2 (i.e., facing to the first shaft 5), as will be apparent from FIGS. 6 and 7. At the second station 7, the diapers 50 held on the first load-carrying tables 16a have the waist-surrounding upper end zones 53 facing inward as viewed in the radial direction of the rotary table 2 (i.e., facing to the first shaft 5) like as in the first station 6 while the diapers 50 held on the second load-carrying tables 16b have the waist-surrounding upper end zones 53 facing outward as viewed in the radial direction of the rotary table 2 (i.e., facing to the peripheral zone 2a of the rotary table 2). In the second station 7, the waist-surrounding upper end zones 53 of the diapers 50 held on the second load-carrying tables 16b have been rotated substantially by an angle of 180° relative to the waist-surrounding upper end zones 53 of the diapers 50 held on the first load-carrying tables 16a (i.e., turn-round by an angle of 180°). The diapers 50 conveyed by the second and fourth conveyor belt assemblies 4, 37 are divided by a counter (not shown) into groups each comprising a predetermined number of the diapers 50 so that the diapers 50 may be conveniently packed in a package 65 as will be described later more in detail.

In the turning-round apparatus 1A, rotation of the rotary table 2 causes the load-carrying tables 16a, 16b to move along the peripheral zone 2a of the rotary table 2 and at the same time to rotate around their own axes in the peripheral zone 2a. In other words, each pair of the adjacent diapers 50 can be rotated by an angle of 180° relative to each other at the second station 7 so that the diapers 50 conveyed by the conveyor belt assemblies 3, 4 at the regular intervals can be alternately turned round.

Figure 8:
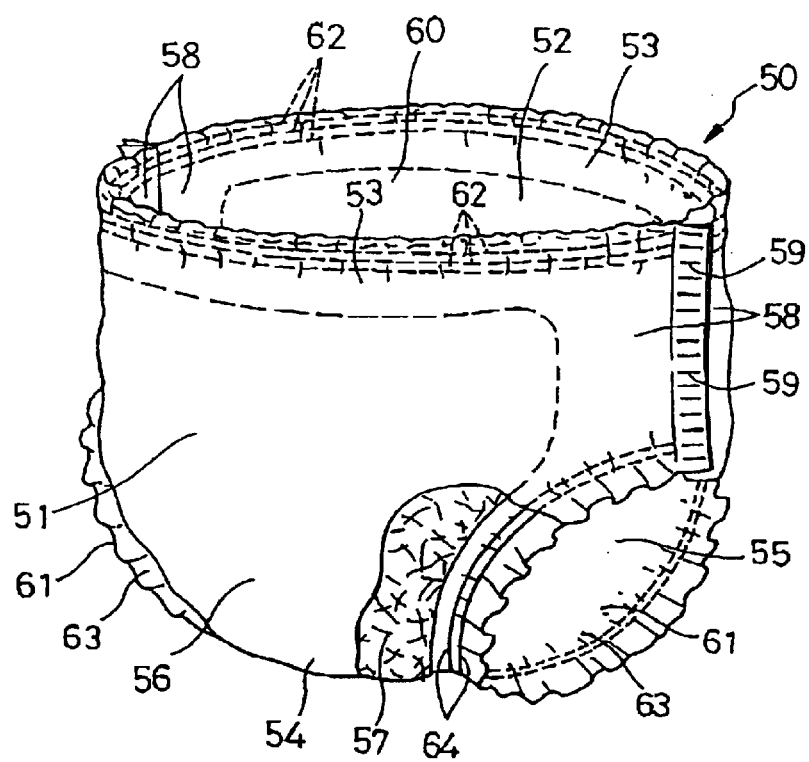
FIG. 8 is a partially cut away perspective view showing a diaper as a specific example of the article.
Figure 9:
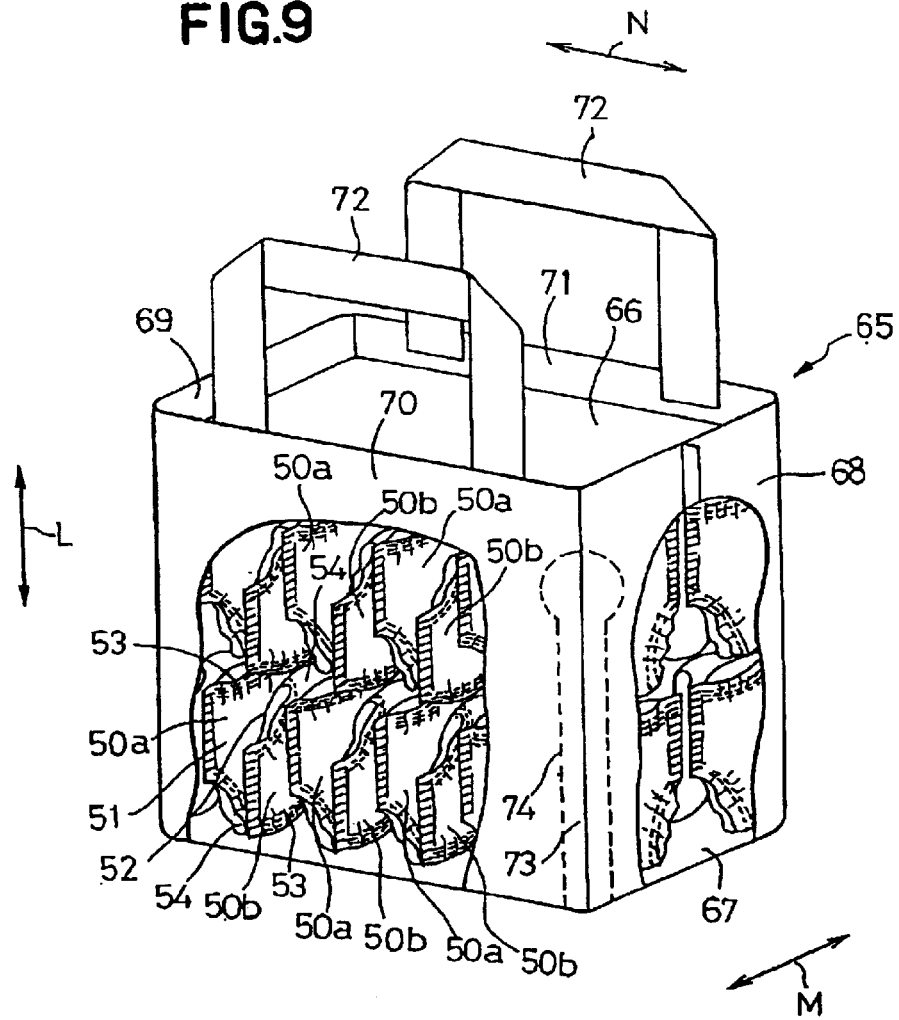
FIG. 9 is a partially cut away perspective view showing a packaged assembly comprising a package and a plurality of diapers as the specific example of the article packaged therein.

FIG. 8 is a partially cut away perspective view showing the diaper 50 as a specific example of the article and FIG. 9 is a partially cut away perspective view showing a packaged assembly comprising the package 65 and a plurality of the diapers 50 each as the specific example of the article. In FIG. 9, a vertical direction is indicated by an arrow L, a horizontal direction is indicated by an arrow M and a back-and-forth direction is indicated by an arrow N.

The diaper 50 comprises a liquid-pervious topsheet 55 facing a wearer's body, a liquid-impervious backsheet 56 facing away from the wearer's body and a liquid-absorbent core 57 interposed between these top- and backsheets 55, 56 and bonded to the inner surfaces of these sheets 55, 56. The front and rear waist regions 51, 52 of the diaper 50 are overlaid along transversely opposite waist lateral zones 58 and joined together by a plurality of heat-sealing lines 59 arranged intermittently along the transversely opposite waist lateral zones 58.

The diaper 50 is formed with a waist-hole 60 and a pair of leg-holes 61 lying below the waist-hole 60. The diaper 50 has the waist-surrounding upper end zone 53 and the crotch bottom zone 54 opposed to the waist-surrounding upper end zone 53. A plurality of waist elastic members 62 are attached to the waist-surrounding upper end zone 53 so that these elastic members 62 extend along the waist-hole 60 and can contract in this direction. A plurality of leg elastic members 64 are attached to leg-hole peripheral zones 63 so that these elastic members 64 extend along the respective leg-holes 61 and can contract in this direction. Portions of the top- and backsheets 55, 56 extending outward beyond a peripheral edge of the core 57 are overlaid and intermittently joined together.

The package 65 is formed by a flexible sheet and presents a substantially regular hexahedron which is relatively long in the back-and-forth direction and each pair of adjacent surfaces of which is orthogonal to each other. The package 65 is contoured by vertically opposed top and bottom surfaces 66, 67, first and second lateral surfaces 68, 69 opposed to each other in the back-and-forth direction, and transversely opposed third and fourth lateral surfaces 70, 71. The third and fourth lateral surfaces 70, 71 are provided with a pair of handling straps 72 describing circular arcs which are convex toward above the package 65. A corner 73 along which the first lateral surface 68 and the third lateral surface 70 intersect with each other is formed with perforations 74 extending in the vertical direction. In the case of the package 65, a region surrounded by the perforations 74 may be torn off from the package 65 to form this corner 73 with a dispensing port for the individual diapers 50.

First diapers 50a transferred from the first conveyor belt assembly 3 onto the first load-carrying tables 16a and second diapers 50b transferred from the first conveyor belt assembly 3 onto the second load-carrying tables 16b are closely packed into a space defined between the first lateral surface 68 and the second lateral surface 69 in a manner that these diapers 50a, 50b may be placed against one another in the back-and-forth direction. In the package 65, these diapers 50a, 50b are alternately arranged so that the each of the second diapers 50b may be interposed between each pair of the diapers 50a.

Within the package 65, the front waist region 51 of the adjacent diapers 50a and the rear waist regions 52 of the diapers 50b are placed against each other under in a compression state. Within the package 65, two groups each comprising a predetermined number of the diapers 50 are placed upon each other in the vertical direction and such two groups are placed side by side. In this manner, four groups of the diapers 50a, 50b are packed in the package 65. The first diapers 50a have their waist-surrounding upper end zones 53 put aside relative to their crotch bottom zones 54 toward the top surface 66 of the package 65. The second diapers 50b have their waist-surrounding upper end zones 53 put aside relative to their crotch bottom zones 54 toward the bottom surface 67 of the package 65.

Figure 10:
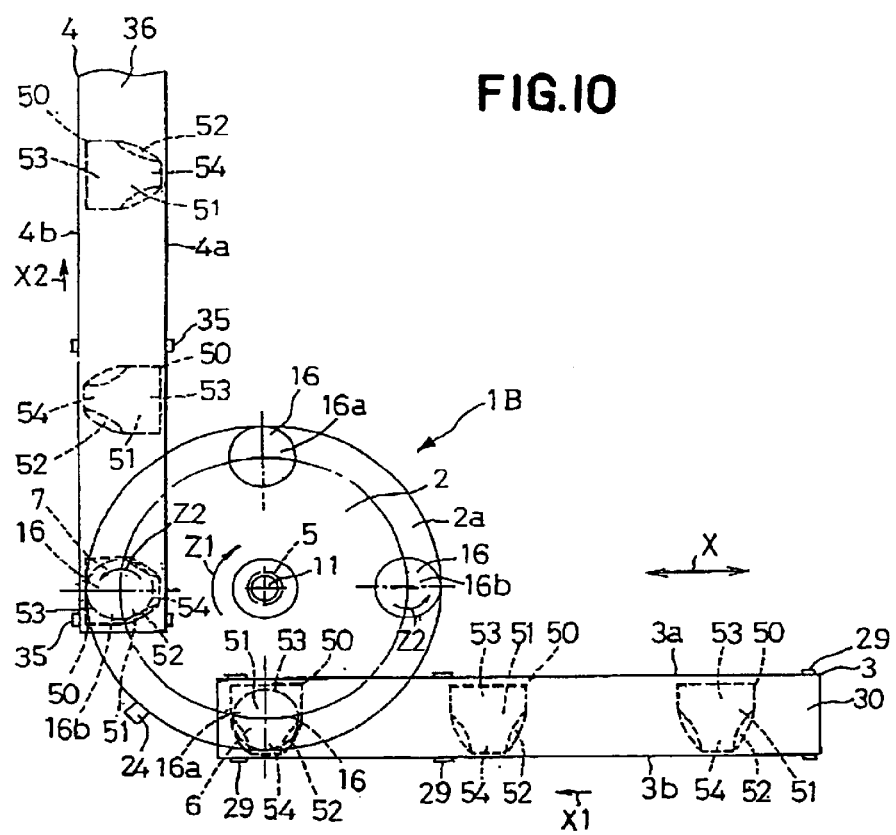
FIG. 10 is a top view showing the article turning-round apparatus according to a preferred embodiment of the invention.
Figure 11:
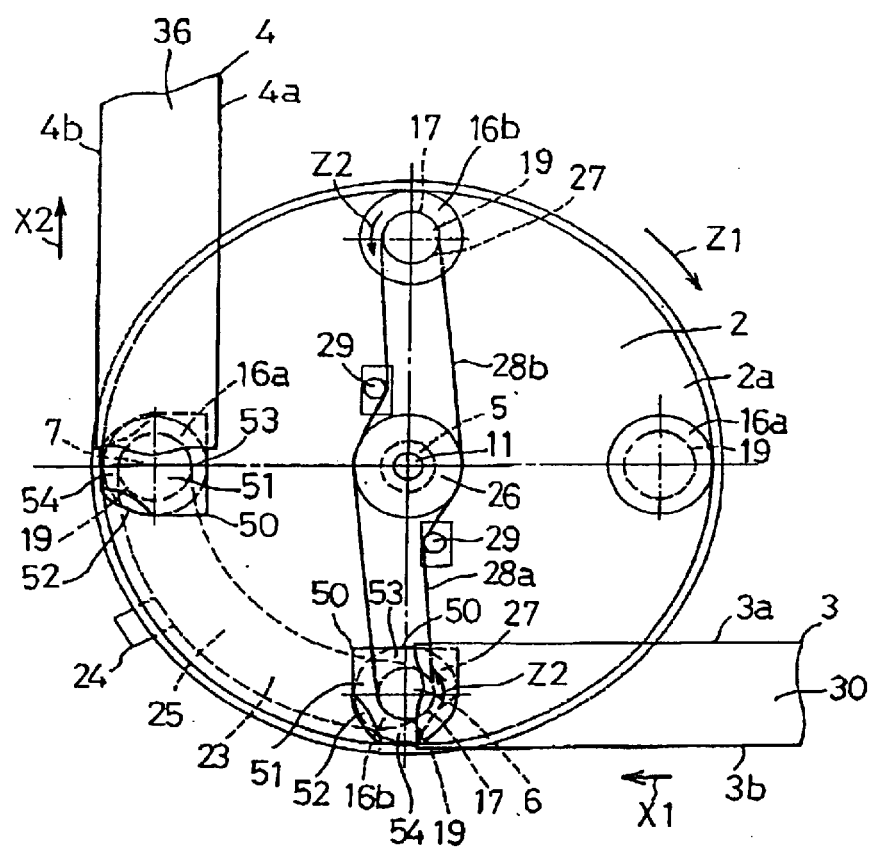
FIG. 11 is a partially cutaway scale-enlarged top view showing the article turning-round apparatus of FIG. 10 with the first and second conveyor belt assemblies.
Figure 12:
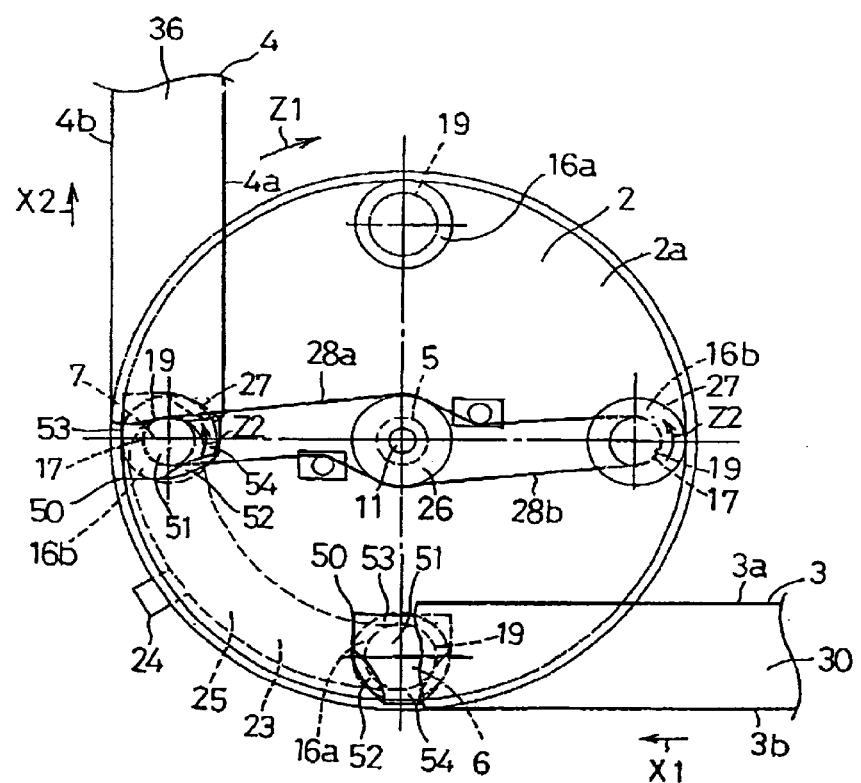
FIG. 12 is a partially cutaway scale-enlarged top view showing the article turning-round apparatus of FIG. 10 with the first and second conveyor belt assemblies.

FIG. 10 is a top view showing the article turning-round apparatus 1B according to a preferred embodiment of the invention, FIG. 11 is a scale-enlarged top view showing the turning-round apparatus 1B of FIG. 10 with first and second conveyor belt assemblies 3, 4 partially cut away and FIG. 12 is also a scale-enlarged top view showing the turning-round apparatus 1B of FIG. 10 with the first and second conveyor belt assemblies 3, 4 partially cut away. In FIG. 10, timing belts 28a, 28b are not shown and, in FIGS. 11 and 12, suction boxes 34, 40 are not shown. FIG. 11 illustrates second load-carrying tables 16b having reached a first station 6 of a rotary table 2 and first load-carrying tables 16a having reached a second station 7. FIG. 12 illustrates the first load-carrying tables 16a having reached the first station 6 of the rotary table 2 and the second load-carrying tables 16b having reached the second station 7 of the rotary table 2.

The turning-round apparatus 1B comprises the rotary table 2(rotary base) provided with a plurality of the load-carrying tables 16, the first conveyor belt assembly 3 serving to convey the diapers 50 onto the rotary table 2 and the second conveyor belt assembly 4 serving to convey the diapers 50 away from the rotary table 2.

The rotary table 2 rotates around a first shaft 5. A peripheral zone 2a of the rotary table 2 is provided with the first station 6 at which the diapers 50 are loaded from the first conveyor belt assembly 3 onto the rotary table 2 and the second station 7 at which the diapers 50 are unloaded from the rotary table 2 onto the second conveyor belt assembly 4. The second station 7 corresponds to a position along the peripheral zone 2a of the rotary table 2 at which the rotary table 2 has been rotated by an angle of 90° from the first station 6 (i.e., the second station 7 is located at an angular distance of 90° from the first station 6). The first shaft 5 has its peripheral surface covered with a stationary frame 9 and contains a stationary shaft 11 inserted through the first shaft 5. A rotational force is transmitted from an electric motor by means of a drive belt 15 to the first shaft 5 so as to be rotated between the stationary frame 9 and the stationary shaft 11 (See FIG. 4). The stationary shaft 11 can not rotate since its lower end 11a is connected with a locking member 13. Rotation of the first shaft 5 causes the rotary table 2 to rotate in the same direction as the direction in which the first shaft 5 rotates.

The load-carrying tables 16 are mounted on the upper surface of the rotary table 2 along the peripheral zone 2a at regular intervals in the circumferential direction of the rotary table 2. The load-carrying tables 16 comprise first load-carrying tables 16a stationarily mounted on the rotary table 2 and second load-carrying tables 16b mounted on the rotary table 2 so as to be rotatable around the second shaft 17 (i.e., around the ducts 19). These first and second load-carrying tables 16a, 16b are alternately arranged along the peripheral zone 2a of the rotary table 2.

The first load-carrying tables 16a move along the peripheral zone 2a of the rotary table 2 as the rotary table 2 rotates. The second load-carrying tables 16b also move along the peripheral zone 2a of the rotary table 2 as the rotary table 2 rotates but simultaneously rotate around their own axes by means of the respective second shafts 17. The first and second load-carrying tables 16a, 16b have a first suction mechanism. The first suction mechanism is same as that illustrated in FIG. 4, wherein the air within the ducts 19 is sucked through the duct 24 into a suction box 23 and a pressure within inner spaces of the respective ducts 19 is maintained at a negative level.

An upper end 11b of the stationary shaft 11 and the second shafts 17 (i.e., the ducts 19) of the second load-carrying tables 16b are provided thereon with pulleys 26, 27. Timing belts 28a, 28b are passed on these pulleys 26, 27. Specifically, these belts 28a, 28b are passed on the pulleys 26, 27 in open fashion. When the rotary table 2 rotates clockwise (in a direction indicated by an arrow Z1), a turning force is transmitted by the belts 28a, 28b to the pulley 27 and thereby the second load-carrying tables 16b rotate counterclockwise (in a direction indicated by an arrow Z2) together with the respective ducts 19 around their own axes.

The first conveyor belt assembly 3 comprises a plurality of belt pulleys 29 and a belt 30 passed on these belt pulleys 29. Below the first conveyor belt assembly 3, a third conveyor belt assembly 31 comprising a plurality of belt pulleys 32 and a belt 33 passed on these belt pulleys 32 is located. The belt 33 circularly runs in synchronization with the belt 30. The first conveyor belt assembly 3 reaches the first station 6 on the upper surface of the rotary table 2. The third conveyor belt assembly 31 terminates short of the peripheral zone 2a of the rotary table 2 (See FIG. 2).

The first conveyor belt assembly 3 is provided with a second suction mechanism serving to suck the diapers 50 and thereby to hold them. The second suction mechanism is similar to that illustrated in FIG. 2 in that the air is sucked into the suction box 34 so that the air may flow from the outer surface to the inner surface of the belt 30 and thereby a suction force is generated through the belt 30. The diapers 50 are held between the first conveyor belt assembly 3 and the third conveyor belt assembly 31 and conveyed at the regular intervals in this state to the first station 6 of the rotary table 2. On the conveyor belt assembly 3, the waist-surrounding upper end zones 53 of the diapers 50 are drawn up in line and the crotch bottom zones 54 of the diapers 50 are drawn up in line.

The second conveyor belt assembly 4 comprises a plurality of belt pulleys 35 and a belt 36 passed on these belt pulleys 35. Below the second conveyor belt assembly 4, a fourth conveyor belt assembly 37 comprising a plurality of belt pulleys 38 and a belt 39 passed on these belt pulleys 38 is located. The belt 39 circularly runs in synchronization with the belt 36. The second conveyor belt assembly 4 reaches the second station 7 on the upper surface of the rotary table 2. The fourth conveyor belt assembly 37 terminates short of the peripheral zone 2a of the rotary table 2 (See FIG. 3).

The second conveyor belt assembly 4 is provided with a third suction mechanism serving to suck the diapers 50 and thereby to hold them. The third suction mechanism is similar to that illustrated in FIG. 3 in that the air is sucked into the suction box 40 so that the air may flow from the outer surface toward the inner surface of the belt 36 and thereby a suction force is generated through the belt 36. The diapers 50 are held between the second conveyor belt assembly 4 and the fourth conveyor belt assembly 37 and conveyed at the regular intervals in this state from the second station 7 outward of the rotary table 2. On the conveyor belt assembly 4, the waist-surrounding upper end zones 53 and the crotch bottom zones 54 of each pair of the adjacent diapers 50 are lined up with one another.

In this turning-round apparatus 1B, in parallel with conveyance of the diapers 50 to the first station 6 by means of those conveyor belt assemblies, any one of the first load-carrying tables 16a or the second load-carrying tables 16b reaches the first station 6. Thereupon the first suction mechanism for the load-carrying table 16a or 16b is actuated. In the turning-round apparatus 1B, the first suction mechanism effectively functions against the effect of the second suction mechanism so that, at the first station 6, the diaper 50 is transferred from the conveyor belt assembly 3 onto the load-carrying table 16a or 16b and held on the load-carrying table 16a or 16b under the suction effect The first load-carrying tables 16a and the second load-carrying tables 16b carrying the diapers 50 thereon, respectively, move from the first station 6 toward the second station 7 of the rotary table 2 as the rotary table 2 rotates clockwise (i.e., in the direction Z1). In the course of traveling from the first station 6 to the second station 7, the second load-carrying tables 16b rotate counterclockwise (i.e., in the direction Z2) on their own axes.

The pulley 26 mounted on the stationary shaft 11 and the pulleys 27 mounted on the respective second shafts 17 (the ducts 19) of the second load-carrying tables 16b rotate at an effective radius ratio (a rotational velocity ratio) of 2:1. With such setting, when the second load-carrying tables 16b move from the first station 6 to the second station 7 along the peripheral zone 2a of the rotary table 2 approximately by an angle of 90°, the second load-carrying tables 16b rotate around their own axes together with the respective ducts 19 approximately by an angle of 180° in the peripheral zone 2a of the rotary table 2.

At the first station 6, the diapers 50 held on the first and second load-carrying tables 16a, 16b, respectively, have the waist-surrounding upper end zones 53 facing inward as viewed in the radial direction of the rotary table 2 (i. e., facing to the first shaft 5), as will be apparent from FIGS. 11 and 12. At the second station 7, the diapers 50 held on the first load-carrying tables 16a have the waist-surrounding upper end zones 53 facing inward as viewed in the radial direction of the rotary table 2 (i.e., facing to the first shaft 5) like as in the first station 6 while the diapers 50 held on the second load-carrying tables 16b have the waist-surrounding upper end zones 53 facing outward as viewed in the radial direction of the rotary table 2 (i.e., facing to the peripheral zone 2a of the rotary table 2). In the second station 7, the waist-surrounding upper end zones 53 of the diapers 50 held on the second load-carrying tables 16b have been rotated substantially by an angle of 180° relative to the waist-surrounding upper end zones 53 of the diapers 50 held on the first load-carrying tables 16a (i.e., turn-round by an angle of 180°).

The diapers 50 are transferred from the load-carrying tables 16a, 16b onto the second conveyor belt assembly 4 under the effect of the third suction mechanism as these load-carrying tables 16a, 16b reach the second station 7. The diapers 50 are held on the conveyor belt assembly 4 under the suction effect with their front waist regions 51 thereof kept in contact with the second conveyor belt assembly 4. In this turning-on apparatus 1B, the third suction mechanism can effectively function against the effect of the first suction mechanism and thereby allows the diapers 50, at the second station, to be quickly transferred from the respective load-carrying tables 16a, 16b onto the conveyor belt assembly 4.

After the diapers 50 have been transferred onto the second conveyor belt assembly 4, the load-carrying tables 16a, 16b move from the second station 7 toward the first station 6 as the rotary table 2 rotates. The second load-carrying tables 16b rotate around their own axes approximately by an angle of 180° in the peripheral zone 2a of the rotary table 2 as these second load-carrying tables 16b move along the peripheral zone 2a of the rotary table 2 approximately by an angle of 90°. In other words, the second load-carrying tables 16b rotate around their own axes approximately by an angle of 540° in the peripheral zone 2a of the rotary table 2 in the course of movement from the second station 7 to the first station 6. More specifically, these second load-carrying tables 16b rotate counterclockwise (i.e., in the direction Z2) around their own axes approximately by an angle of 720° in the peripheral zone 2a of the rotary table 2 as the rotary table 2 rotates clockwise (i.e., in the direction Z1) by an angle of 360°. The diapers 50 having been conveyed by the second and fourth conveyor belt assemblies 4, 37 are divided into groups each comprising a predetermined number of the diapers 50 by the counter in the same manner as has been described in reference with FIG. 1 so that the diapers 50 may be conveniently packed in the package 65 (See FIG. 9).

This turning-round apparatus 1B has the second station 7 at the angular distance of 90° from the first station 6, which is substantially smaller than the angular distance between the first and second stations 6, 7 in the apparatus illustrated in FIG. 1. Assumed that the rotary table 2 in this turning-round apparatus 1B rotates at the same velocity as in the turning-round apparatus illustrated in FIG. 1, the time taken for movement of the load-carrying tables 16a, 16b from the first station 6 to the second station 7 can be shortened relative to the case of the embodiment illustrated in FIG. 1 and correspondingly the diapers 50 can be further quickly turned round. Placement of the second station 7 at the angular distance of 90° from the first station 6 allows the direction in which the diapers 50 are conveyed by the second conveyor belt assembly 4 (the direction X2) to be turned by an angle of 90° relative to the direction in which the diapers 50 are conveyed by the first conveyor belt assembly 3 (the direction X1).

Figure 13:
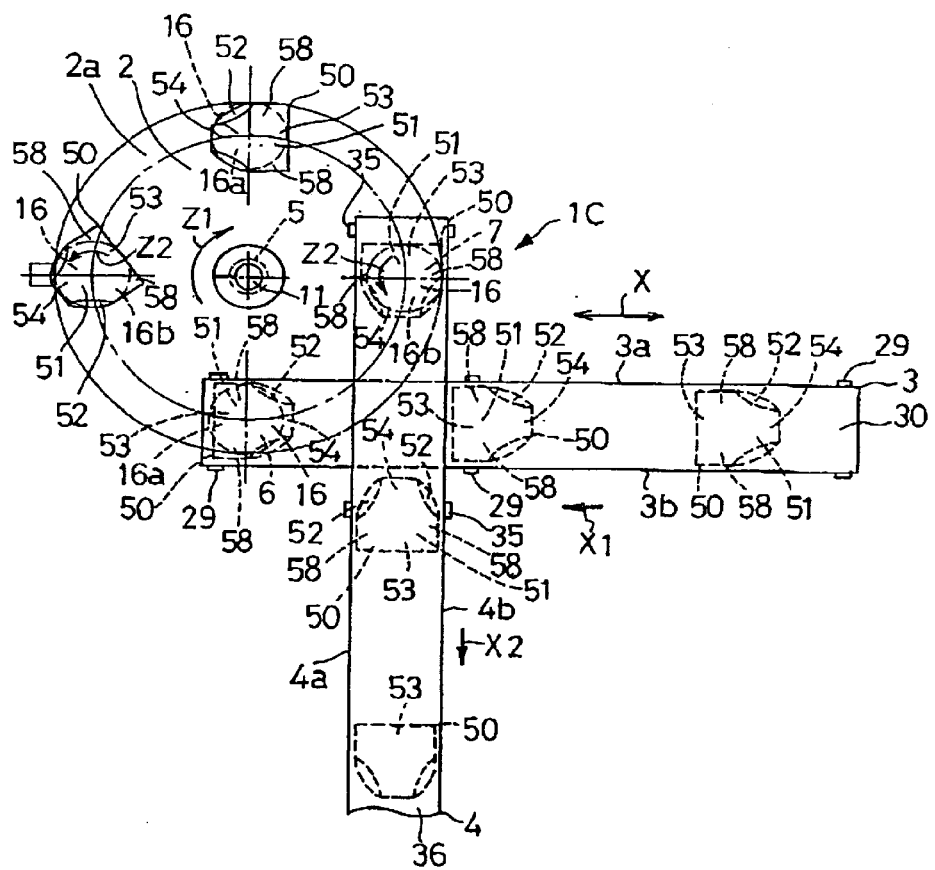
FIG. 13 is a top view showing the article turning-round apparatus according to still another embodiment of the invention.
Figure 14:
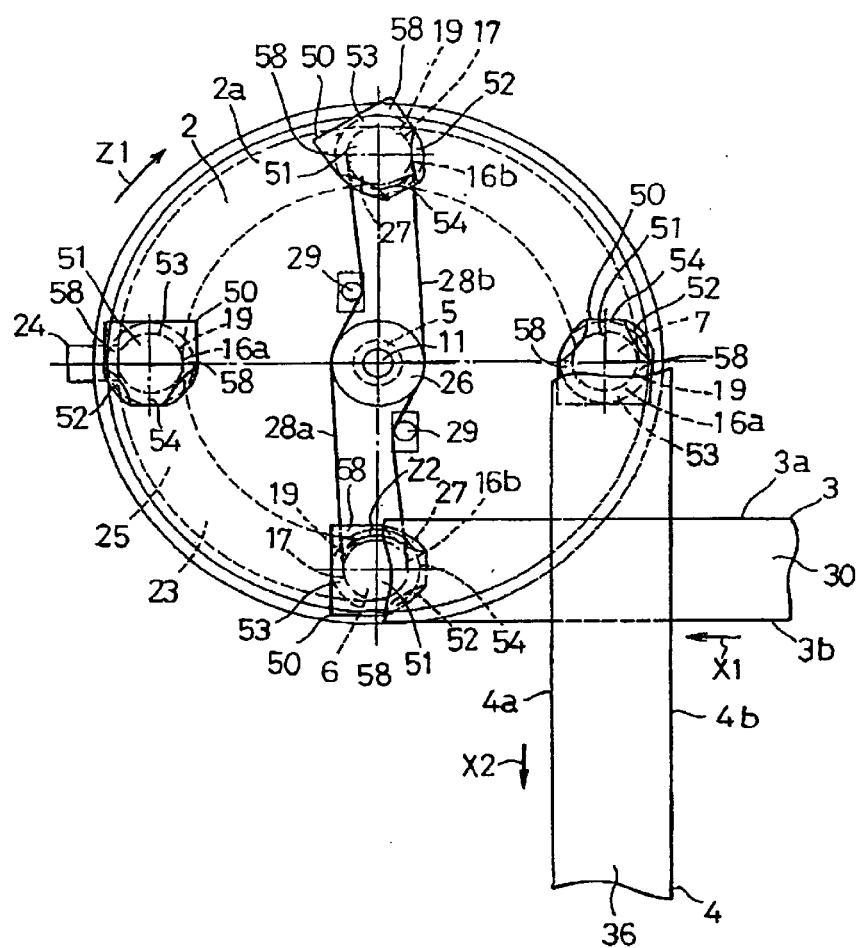
FIG. 14 is a partially cutaway scale-enlarged top view showing the article turning-round apparatus of FIG. 13 with the first and second conveyor belt assemblies.
Figure 15:
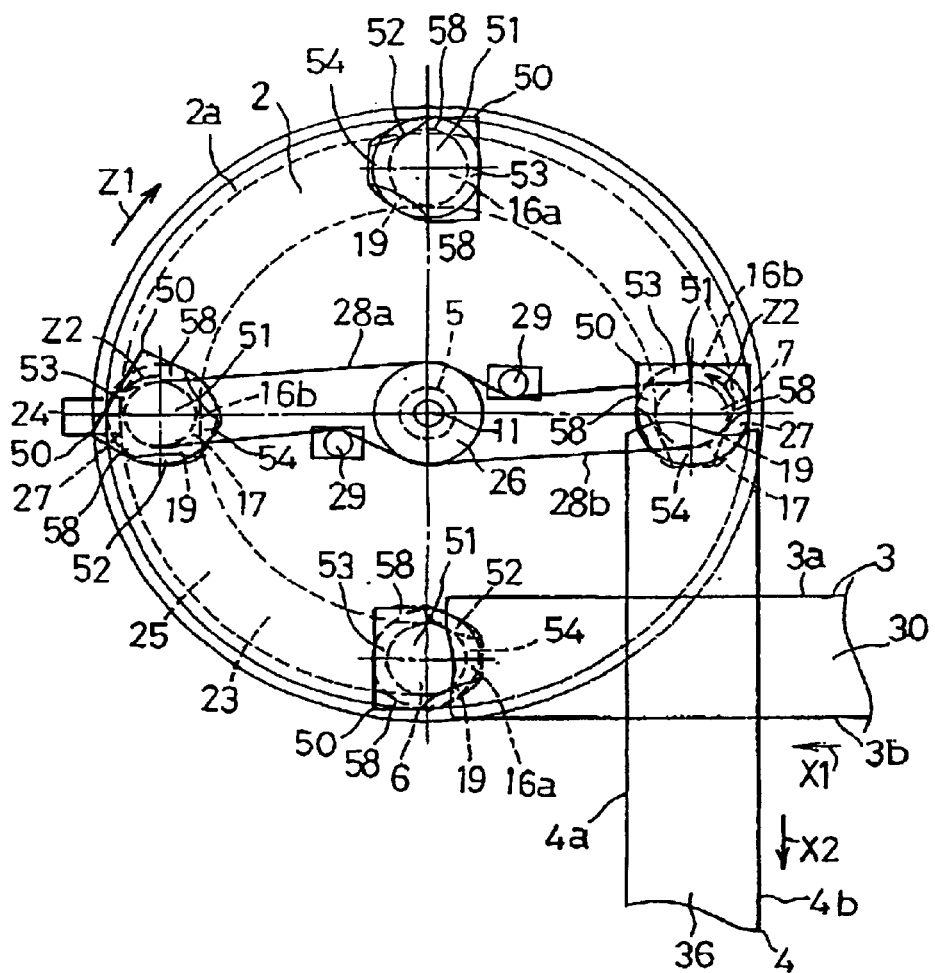
FIG. 15 is a partially cutaway scale-enlarged top view showing the article turning-round apparatus of FIG. 13 with the first and second conveyor belt assemblies.

FIG. 13 is a top view showing the article turning-round apparatus 1C according to still another embodiment of the invention, FIG. 14 is a scale-enlarged top view showing the article turning-round apparatus 1C of FIG. 13 with the first and second conveyor belt assemblies 3, 4 partially cut away and FIG. 15 also is a scale-enlarged top view showing the article turning-round apparatus 1C of FIG. 13 with the first and second conveyor belt assemblies 3, 4 partially cut away. In FIG. 13, the timing belts 28a, 28b are not shown and, in FIGS. 14 and 15, the suction boxes 34, 40 are not shown. FIG. 14 illustrates second load-carrying tables 16b having reached a first station 6 of the rotary table 2 and the first load-carrying tables 16a having reached a second station 7 of the rotary table 2. FIG. 15 illustrates the first load-carrying tables 16a having reached the first station 6 of the rotary table 2 and the second load-carrying tables 16b having reached the second station 7 of the rotary table 2.

The turning-round apparatus 1C comprises the rotary table 2(rotary base) provided with a plurality of the load-carrying tables 16, the first conveyor belt assembly 3 serving to convey the diapers 50 onto the rotary table 2 and the second conveyor belt assembly 4 serving to convey the diapers 50 away from the rotary table 2.

The rotary table 2 rotates around a first shaft 5. A peripheral zone 2a of the rotary table 2 is provided with the first station 6 at which the diapers 50 are loaded from the first conveyor belt assembly 3 onto the rotary table 2 and the second station 7 at which the diapers 50 are unloaded from the rotary table 2 onto the second conveyor belt assembly 4. The second station 7 corresponds to a position along the peripheral zone 2a of the rotary table 2 at which the rotary table 2 has been rotated by an angle of 270° from the first station 6 (i.e., the second station 7 is located at an angular distance of 270° from the first station 6). The first shaft 5 has its peripheral surface covered with a stationary frame 9 and contains a stationary shaft 11 inserted through the first shaft 5. A rotational force is transmitted from an electric motor by means of a drive belt 15 to the first shaft 5 so as to be rotated between the stationary frame 9 and the stationary shaft 11 (See FIG. 4). The stationary shaft 11 can not rotate since its lower end 11a is connected with a locking member 13 Rotation of the first shaft 5 causes the rotary table 2 to rotate in the same direction as the direction in which the first shaft 5 rotates.

The load-carrying tables 16 are mounted on the upper surface of the rotary table 2 along the peripheral zone 2a at regular intervals in the circumferential direction of the rotary table 2. The load-carrying tables 16 comprise first load-carrying tables 16a stationarily mounted on the rotary table 2 and second load-carrying tables 16b mounted on the rotary table 2 so as to be rotatable around the second shaft 17 (i.e., around the ducts 19). These first and second load-carrying tables 16a, 16b are alternately arranged along the peripheral zone 2a of the rotary table 2.

The first load-carrying tables 16a move along the peripheral zone 2a of the rotary table 2 as the rotary table 2 rotates. The second load-carrying tables 16b also move along the peripheral zone 2a of the rotary table 2 as the rotary table 2 rotates but simultaneously rotate around their own axes by means of the respective second shafts 17. The first and second load-carrying tables 16a, 16b have a first suction mechanism. The first suction mechanism is same as that illustrated in FIG. 4, wherein the air within the ducts 19 is sucked through the duct 24 into a suction box 23 and a pressure within inner spaces of the respective ducts 19 is maintained at a negative level.

Upper end 11b of the stationary shaft 11 and the second shafts 17 (i.e., the ducts 19) of the second load-carrying tables 16b are provided thereon with pulleys 26, 27. Timing belts 28a, 28b are passed on these pulleys 26, 27. Specifically, these belts 28a, 28b are passed on the pulleys 26, 27 in open fashion. When the rotary table 2 rotates clockwise (in a direction indicated by an arrow Z1), a turning force is transmitted by the belts 28a, 28b to the pulley 27 and thereby the second load-carrying tables 16b rotate counterclockwise (in a direction indicated by an arrow Z2) together with the respective ducts 19 around their own axes.

The first conveyor belt assembly 3 comprises a plurality of belt pulleys 29 and a belt 30 passed on these belt pulleys 29. Below the first conveyor belt assembly 3, a third conveyor belt assembly 31 comprising a plurality of belt pulleys 32 and a belt 33 passed on these belt pulleys 32 is located. The belt 33 circularly runs in synchronization with the belt 30. The first conveyor belt assembly 3 reaches the first station 6 on the upper surface of the rotary table 2. The third conveyor belt assembly 31 terminates short of the peripheral zone 2a of the rotary table 2 (See FIG. 2).

The first conveyor belt assembly 3 is provided with a second suction mechanism serving to suck the diapers 50 and thereby to hold them. The second suction mechanism is similar to that illustrated in FIG. 2 in that the air is sucked into the suction box 34 so that the air may flow from the outer surface to the inner surface of the belt 30 and thereby a suction force is generated through the belt 30. The diapers 50 are held between the first conveyor belt assembly 3 and the third conveyor belt assembly 31 and conveyed at the regular intervals in this state to the first station 6 of the rotary table 2. On the conveyor belt assembly 3, the waist-surrounding upper end zones 53 of each pair of the adjacent diapers 50 are drawn up in line and the crotch bottom zones 54 of each pair of the adjacent diapers 50 are opposed to each other and the transversely opposite waist lateral zones 58 of the diapers 50 extend parallel to inner and outer side edges 3a, 3b of the conveyor belt assembly 3.

The second conveyor belt assembly 4 comprises a plurality of belt pulleys 35 and a belt 36 passed on these belt pulleys 35. Below the second conveyor belt assembly 4, a fourth conveyor belt assembly 37 comprising a plurality of belt pulleys 38 and a belt 39 passed on these belt pulleys 38 is located. The belt 39 circularly runs in synchronization with the belt 36. The second conveyor belt assembly 4 reaches the second station 7 on the upper surface of the rotary table 2. The fourth conveyor belt assembly 37 terminates short of the peripheral zone 2a of the rotary table 2 (See FIG. 3).

The second conveyor belt assembly 4 is provided with a third suction mechanism serving to suck the diapers 50 and thereby to hold them. The third suction mechanism is similar to that illustrated in FIG. 3 in that the air is sucked into the suction box 40 so that the air may flow from the outer surface toward the inner surface of the belt 36 and thereby a suction force is generated through the belt 36. The diapers 50 are held between the second conveyor belt assembly 4 and the fourth conveyor belt assembly 37 and conveyed at the regular intervals in this state from the second station 7 outward of the rotary table 2. On the convey or belt assembly 4, the waist-surrounding upper end zones 53 of each pair of the adjacent diapers 50 are opposed to each other, the crotch bottom zones 54 of each pair of the adjacent diapers 50 are opposed to each other and the transversely opposite waist lateral zones 58 extend parallel to inner and outer side edges 4a, 4b of the conveyor belt assembly 4.

In this turning-round apparatus 1C, in parallel with conveyance of the diapers 50 to the first station 6 by means of those conveyor belt assemblies 3, 31, any one of the first load-carrying tables 16a or the second load-carrying tables 16b reaches the first station 6. Thereupon the first suction mechanism for the load-carrying table 16a or 16b is actuated. In the turning-round apparatus 1C, the first suction mechanism effectively functions against the effect of the second suction mechanism so that, at the first station 6, the diaper 50 is transferred from the conveyor belt assembly 3 onto the load-carrying table 16a or 16b and held on the load-carrying table 16a or 16b under the suction effect.

The first load-carrying tables 16a and the second load-carrying tables 16b carrying the diapers 50 thereon, respectively, move from the first station 6 toward the second station 7 of the rotary table 2 as the rotary table 2 rotates clockwise (i.e., in the direction Z1). In the course of traveling from the first station 6 to the second station 7, the second load-carrying tables 16b rotate counterclockwise (i.e., in the direction Z2) on their own axes.

The pulley 26 mounted on the stationary shaft 11 and the pulleys 27 mounted on the respective second shafts 17 (the ducts 19) of the second load-carrying tables 16b rotate at an effective radius ratio (a rotational velocity ratio) of 2:3. With such setting, when the second load-carrying tables 16b move from the first station 6 to the second station 7 along the peripheral zone 2a of the rotary table 2 approximately by an angle of 270°, the second load-carrying tables 16b rotate around their own axes together with the respective ducts 19 approximately by an angle of 180° in the peripheral zone 2a of the rotary table 2.

At the first station 6, the waist-surrounding upper end zones 53 of the diapers 50 held on the first and second load-carrying tables 16a, 16b face to the conveyance direction of the diapers 50 on the conveyor belt assembly 3 (the direction X1) as will be apparent from FIGS. 14 and 15. At the second station 7, the waist-surrounding upper end zones 53 of the diapers 50 held on the first load-carrying tables 16a face to the conveyance direction of the diapers 50 on the conveyor belt assembly 4 (the direction X2) while the crotch bottom zones 53 of the diapers 50 held on the second load-carrying tables 16b face to the conveyance direction of the diapers 50 on the conveyor belt assembly 4 (the direction X2). In the second station 7, the waist-surrounding upper end zones 53 of the diapers 50 held on the second load-carrying tables 16b have been rotated substantially by an angle of 180° relative to the waist-surrounding upper end zones 53 of the diapers 50 held on the first load-carrying tables 16a.

The diapers 50 are transferred from the load-carrying tables 16a, 16b onto the second conveyor belt assembly 4 under the effect of the third suction mechanism as these load-carrying tables 16a, 16b reach the second station 7. The diapers 50 have their front waist regions 51 sucked and held on the conveyor belt assembly 4. In this turning-round apparatus 1C, the third suction mechanism can effectively function against the effect of the first suction mechanism and thereby allows the diapers 50, at the second station 7, to be quickly transferred from the respective load-carrying tables 16a, 16b onto the conveyor belt assembly 4.

After the diapers 50 have been transferred onto the second conveyor belt assembly 4, the load-carrying tables 16a, 16b move from the second station 7 toward the first station 6 as the rotary table 2 rotates. The second load-carrying tables 16b rotate around their own axes approximately by an angle of 180° in the peripheral zone 2a of the rotary table 2 as these second load-carrying tables 16b move along the peripheral zone 2a of the rotary table 2 approximately by an angle of 270°. In other words, the second load-carrying tables 16b rotate approximately by 60° around their own axes in the peripheral zone 2a of the rotary table 2 in the course of movement from the second station 7 to the first station 6. More specifically, these second load-carrying tables 16b rotate counterclockwise (i.e., in the direction Z2) around their own axes approximately by an angle of 240° in the peripheral zone 2a of the rotary table 2 as the rotary table 2 rotates clockwise (i.e., in the direction Z1) by an angle of 360°. The diapers 50 having been conveyed by the second and fourth conveyor belt assemblies 4, 37 are divided into groups each comprising a predetermined number of the diapers 50 by the counter in the same manner as has been described in reference with FIG. 1 so that the diapers 50 may be conveniently packed in the package 65 (See FIG. 9).

The turning-round apparatuses 1A, 1B, 1C are applicable not only to turn round the pull-on diaper 50 but also to turn round the other wearing articles such as pull-on diaper covers and open-type diapers having front and rear waist regions adapted to be connected with each other immediately before put on a wearer's body. In the case of the open-type diapers, each diaper is folded in two along its crotch bottom end zone with the topsheet inside so that the diapers may be transferred in such a folded state from the first conveyor belt assembly 3 onto the load-carrying tables 16a, 16b.

Particularly when the turning-round apparatuses 1A, 1B, 1C are used to turn round the disposable diapers 50, it is not essential for the openings 18 formed through the first and second load-carrying tables 16a, 16b to be distributed so as to be covered with the entire waist region of the diaper 50 so far as these openings 18 are distributed so as to be covered with a domain corresponding to the core 57 of the diaper 50 which has relatively high resistance to the air-permeability.

The article turning-round apparatus according to the present invention is primarily characterized in that rotation of the rotary base causes the load-carrying tables to move along the peripheral zone of the rotary base and simultaneously causes the second load-carrying tables to rotate around their own axes approximately by an angle of 180° relative to the first load-carrying tables in the peripheral zone of the rotary base. With a consequence, each pair of the adjacent articles can be turned round by an angle of 180° relative to each other, i.e., the articles being conveyed at the regular intervals can be alternately turned round. The turning-round apparatus according to the present invention is a construction simplified so that the desired principal function to rotate the second load-carrying tables around their own axes relative to the rotary base can be achieved without making the apparatus bulky and complex.

Furthermore, it is possible for the apparatus to turn round the articles at a high velocity and thereby to turn round a large number of the articles per a predetermined time. The apparatus allows also the position of the second station relative to the first station to be freely set by changing the rotational velocity ratio between the pulleys. In other words, there is no restriction so far as the positions on the rotary base at which the articles are loaded and unloaded, respectively, are concerned and a free layout of the apparatus is ensured.

In this turning-round apparatus, the first and second load-carrying tables include the first suction mechanism functioning to suck and hold the articles so that, in the first station, the articles can be smoothly transferred from the first conveyor belt assembly onto these load-carrying tables. In addition, the articles are reliably held on these load-carrying tables under the suction effect of the first suction mechanism without any possibility that the articles might be driven off from the rotary base due to a centrifugal force generated as the rotary base rotates.

With the turning-round apparatus in which the first conveyor belt assembly includes the second suction mechanism functioning to suck and hold the articles thereon, the first conveyor belt assembly can reliably hold the articles thereon under the suction effect until the articles are conveyed to the first station on the rotary base. With the turning-round apparatus in which the second conveyor belt assembly includes the third suction mechanism functioning to suck and hold the articles, the second conveyor belt assembly can reliably hold the articles thereon under the suction effect and the articles are smoothly transferred, at the second station, to the second conveyor belt assembly.

What is claimed is:

1. An article turning-round apparatus provided with first and second stations at which a plurality of disposable wearing articles each having, in addition to front and rear waist regions opposed to each other, a waist-surrounding upper end zone and a crotch bottom zone, are successively loaded and unloaded, respectively, and adapted to successively turn round said articles moving from said first station to said second station, said article turning-round apparatus being characterized by that:

said turning-round apparatus comprises a rotary base adapted to be rotated by means of a first shaft and provided along a peripheral zone thereof with said first and second stations and a plurality of load-carrying tables arranged at regular intervals along said peripheral zone, said load-carrying tables being adapted to carry thereon said articles of which said front or rear waist regions are held in contact with said load-carrying tables and said waist-surrounding upper end zones are lined up in a predetermined direction;

said load-carrying tables comprise first load-carrying tables adapted to move along said peripheral zone of said rotary base and second load-carrying tables mounted on said rotary base so as to be rotated by respective second shafts extending in an axial direction of said first shaft, said second load-carrying tables being adapted to be rotated around their own axes in said peripheral zone of said rotary base while said second load-carrying tables move along said peripheral zone of said rotary base as said rotary base rotates, said first and second load-carrying tables being alternately arranged so that each of said second load-carrying tables be interposed between each pair of said first load-carrying tables; and said first and second load-carrying tables are successively loaded with said articles as soon as said first and second load-carrying tables alternately reach said first station as said rotary base rotates and said second load-carrying tables rotate in said peripheral zone of said rotary base on their own axes substantially by an angle of 180° relative to said first load-carrying tables while said second load-carrying tables move along said peripheral zone of said rotary base from said first station to said second station.

2. The article turning-round apparatus according to claim 1, wherein said first and second load-carrying tables include a first suction mechanism functioning to hold said articles on said first and second load-carrying tables under a suction effect, said first load-carrying tables move along said peripheral zone of said rotary base from said first station to said second station together with said articles held thereon under the suction effect, on one hand, and said second load-carrying tables rotating around their own axes together with said articles held thereon under the suction effect in said peripheral zone of said rotary base while said second load-carrying tables move along said peripheral zone of said rotary base together with said articles held thereon under the suction effect from said first station to said second station, on the other hand.

3. The article turning-round apparatus according to claim 1, further comprising a first conveyor belt assembly adapted to convey said articles at regular intervals to said first station of said rotary base so that each pair of adjacent said articles may have respective waist-surrounding upper end zones and respective crotch bottom zones opposed to each other and a second conveyor belt assembly adapted to convey said articles away from said second station of said rotary base at regular intervals so that each pair of adjacent said articles may have respective waist-surrounding upper end zones opposed to each other.

4. The article turning-round apparatus according to claim 1, wherein said article is a pull-on disposable diaper comprising a liquid-pervious topsheet facing a wearer's body, a liquid-impervious backsheet facing away from said wearer's body and a liquid-absorbent core interposed between said top- and backsheets and formed with a waist-hole and a pair of leg-holes.

5. The article turning-round apparatus according to claim 1, further comprising a first conveyor belt assembly adapted to convey said articles at regular intervals to said first station of said rotary base so that each pair of adjacent said articles may have respective waist-surrounding upper end zones lined up with each other and a second conveyor belt assembly adapted to convey said articles away from said second station of said rotary base at regular intervals so that each pair of adjacent said articles may have respective waist-surrounding upper end zones and respective crotch bottom zones lined up with each other.

6. The article turning-round apparatus according to claim 5, wherein said first conveyor belt assembly includes a second suction mechanism adapted to hold said articles on said first conveyor belt under a suction effect and, when said first and second load-carrying tables come face to face with said first conveyor belt assembly, said first suction mechanism effectively functions against the effect of said second suction mechanism to transfer said articles from said first conveyor belt assembly onto said first and second load-carrying tables.

7. The article turning-round apparatus according to claim 5, wherein said second conveyor belt assembly includes a third suction mechanism adapted to hold said articles on said second conveyor belt under a suction effect and, when said first and second load-carrying tables come face to face with said second conveyor belt assembly, said third suction mechanism effectively functions against the effect of said first suction mechanism to transfer said articles from said first and second load-carrying tables onto said second conveyor belt assembly.

* * * * *